United States Patent
Sharma et al.

(10) Patent No.: US 7,987,111 B1
(45) Date of Patent: Jul. 26, 2011

(54) METHOD AND SYSTEM FOR CHARACTERIZING PHYSICAL RETAIL SPACES BY DETERMINING THE DEMOGRAPHIC COMPOSITION OF PEOPLE IN THE PHYSICAL RETAIL SPACES UTILIZING VIDEO IMAGE ANALYSIS

(75) Inventors: Rajeev Sharma, State College, PA (US); Satish Mummareddy, Washington, DC (US); Jeff Hershey, Norfolk, VA (US); Hankyu Moon, State College, PA (US)

(73) Assignee: VideoMining Corporation, State College, PA (US)

( * ) Notice: Subject to any disclaimer, the term of this patent is extended or adjusted under 35 U.S.C. 154(b) by 942 days.

(21) Appl. No.: 11/978,021

(22) Filed: Oct. 26, 2007

Related U.S. Application Data

(60) Provisional application No. 60/855,223, filed on Oct. 30, 2006.

(51) Int. Cl.
*G06Q 10/00* (2006.01)

(52) U.S. Cl. ..................................................... 705/7.29

(58) Field of Classification Search ............... 705/7.29
See application file for complete search history.

(56) References Cited

U.S. PATENT DOCUMENTS

| | | | | |
|---|---|---|---|---|
| 4,847,604 A | * | 7/1989 | Doyle | 345/180 |
| 4,972,504 A | | 11/1990 | Daniel, Jr. et al. | |
| 4,975,960 A | * | 12/1990 | Petajan | 704/251 |
| 5,012,522 A | * | 4/1991 | Lambert | 382/118 |
| 5,227,874 A | * | 7/1993 | Von Kohorn | 705/10 |
| 5,315,093 A | | 5/1994 | Stewart | |
| 5,331,544 A | | 7/1994 | Lu et al. | |
| 5,369,571 A | * | 11/1994 | Metts | 705/10 |
| 5,715,325 A | * | 2/1998 | Bang et al. | 382/118 |
| 5,774,868 A | * | 6/1998 | Cragun et al. | 705/7.31 |
| 5,793,281 A | * | 8/1998 | Long | 340/384.1 |
| 5,974,396 A | * | 10/1999 | Anderson et al. | 705/7.33 |

(Continued)

FOREIGN PATENT DOCUMENTS

WO    WO 99/14694    *  3/1999

OTHER PUBLICATIONS

Advancedinterfaces.com Web Pages Advanced Interfaces, Inc., Dec. 2003-Apr. 2004, Retrieved from Archive.org Jan. 18, 2011.*

(Continued)

*Primary Examiner* — Scott L Jarrett

(57) ABSTRACT

The present invention is a method and system for characterizing physical space based on automatic demographics measurement, using a plurality of means for capturing images and a plurality of computer vision technologies. The present invention is called demographic-based retail space characterization (DBR). Although the disclosed method is described in the context of retail space, the present invention can be applied to any physical space that has a restricted boundary. In the present invention, the physical space characterization can comprise various types of characterization depending on the objective of the physical space, and it is one of the objectives of the present invention to provide the automatic demographic composition measurement to facilitate the physical space characterization. The demographic classification and composition measurement of people in the physical space is performed automatically based on a novel usage of a plurality of means for capturing images and a plurality of computer vision technologies on the captured visual information of the people in the physical space. The plurality of computer vision technologies can comprise face detection, person tracking, body parts detection, and demographic classification of the people, on the captured visual information of the people in the physical space.

46 Claims, 20 Drawing Sheets

U.S. PATENT DOCUMENTS

| | | | | |
|---|---|---|---|---|
| 5,995,015 | A * | 11/1999 | DeTemple et al. | 340/5.9 |
| 6,047,078 | A * | 4/2000 | Kang | 382/107 |
| 6,055,573 | A | 4/2000 | Gardenswartz et al. | |
| 6,112,988 | A * | 9/2000 | Powell | 235/383 |
| 6,119,098 | A | 9/2000 | Guyot et al. | |
| 6,123,259 | A * | 9/2000 | Ogasawara | 235/380 |
| 6,182,050 | B1 | 1/2001 | Ballard | |
| 6,184,926 | B1 * | 2/2001 | Khosravi et al. | 348/239 |
| 6,298,330 | B1 | 10/2001 | Gardenswartz et al. | |
| 6,301,370 | B1 * | 10/2001 | Steffens et al. | 382/103 |
| 6,317,718 | B1 * | 11/2001 | Fano | 705/14.39 |
| 6,404,900 | B1 * | 6/2002 | Qian et al. | 382/103 |
| 6,421,463 | B1 | 7/2002 | Poggio et al. | |
| 6,437,819 | B1 * | 8/2002 | Loveland | 348/143 |
| 6,513,015 | B2 * | 1/2003 | Ogasawara | 705/26.1 |
| 6,529,940 | B1 | 3/2003 | Humble | |
| 6,536,658 | B1 * | 3/2003 | Rantze | 235/375 |
| 6,556,832 | B1 * | 4/2003 | Soliman | 455/456.5 |
| 6,563,423 | B2 * | 5/2003 | Smith | 340/572.1 |
| 6,847,969 | B1 | 1/2005 | Mathai et al. | |
| 6,990,217 | B1 | 1/2006 | Moghaddam et al. | |
| 7,003,476 | B1 | 2/2006 | Samra et al. | |
| 7,006,982 | B2 * | 2/2006 | Sorensen | 705/10 |
| 7,227,976 | B1 * | 6/2007 | Jung et al. | 382/103 |
| 7,267,277 | B2 * | 9/2007 | Apte et al. | 235/454 |
| 7,283,650 | B1 * | 10/2007 | Sharma et al. | 382/118 |
| 7,317,812 | B1 * | 1/2008 | Krahnstoever et al. | 382/103 |
| 7,319,479 | B1 * | 1/2008 | Crabtree et al. | 348/169 |
| 7,319,779 | B1 * | 1/2008 | Mummareddy et al. | 382/118 |
| 7,406,437 | B2 * | 7/2008 | Goodwin, III | 705/14.36 |
| 7,415,510 | B1 * | 8/2008 | Kramerich et al. | 709/219 |
| 7,505,621 | B1 * | 3/2009 | Agrawal et al. | 382/159 |
| 7,606,728 | B2 * | 10/2009 | Sorensen | 705/10 |
| 7,617,981 | B2 * | 11/2009 | Apte et al. | 235/454 |
| 7,643,658 | B2 * | 1/2010 | Kilner et al. | 382/118 |
| 7,711,155 | B1 * | 5/2010 | Sharma et al. | 382/118 |
| 7,742,623 | B1 * | 6/2010 | Moon et al. | 382/103 |
| 7,848,548 | B1 * | 12/2010 | Moon et al. | 382/118 |
| 7,921,036 | B1 * | 4/2011 | Sharma et al. | 705/14.66 |
| 7,933,797 | B2 * | 4/2011 | Sorensen | 705/7.31 |
| 2001/0056405 | A1 * | 12/2001 | Muyres et al. | 705/52 |
| 2002/0178085 | A1 * | 11/2002 | Sorensen | 705/26 |
| 2002/0184098 | A1 * | 12/2002 | Giraud et al. | 705/14 |
| 2003/0039379 | A1 * | 2/2003 | Gutta et al. | 382/116 |
| 2003/0088332 | A1 * | 5/2003 | Agostinelli et al. | 715/526 |
| 2003/0110038 | A1 | 6/2003 | Sharma et al. | |
| 2003/0216958 | A1 | 11/2003 | Register et al. | |
| 2004/0128198 | A1 | 7/2004 | Register et al. | |
| 2006/0010028 | A1 * | 1/2006 | Sorensen | 705/10 |
| 2006/0036485 | A1 | 2/2006 | Duri et al. | |
| 2006/0041480 | A1 | 2/2006 | Briggs | |
| 2008/0067244 | A1 * | 3/2008 | Marks | 235/385 |

OTHER PUBLICATIONS

VideoMining.com Web Pages Advanced Interfaces, Inc., Jun. 2004-Feb. 2005, Retrieved from Archive.org Jan. 18, 2011.*

Gaynor, Mark, Hidden Cameras Revel Human Side of P-O-P Story P-O-P Times, 1999.*

Haritaoglu, Ismail et al., Detection and Tracking of Shopping Groups in Stores IEEE, 2001.*

Heller, Walter, Tracking Shoppers Through the Combination Store Progressive Grocer, vol. 67, No. 7, Jul. 1988.*

Pereira, Joseph, Marketing Researchers' Cameras Tracking Shoppers in Stores; Video Miners Tell Merchants Who's Buying and Browsing, Wall Street Journal, Dec. 23, 2004.*

Discovery Channel Discovers Opportunities with Accurate Traffic Data Stores, Dec. 2002.*

ShopperTrak.com Web Pages ShopperTrack, 2003, Retreived from Archive.org Jun. 1, 2010.*

Envirosell.com Web Pages Envirosell, Inc., Mar. 2001, Retrieved from Archive.org Feb. 2008.*

Moghaddam, Baback et al., Gender Classification with Support Vector Machines IEEE, 2002.*

Gutta, Srinivas et al., Gender and Ethinc Classication of Face Images IEEE, 1998.*

Gutta, Srinivas et al., Minxture of Experts for Classification of Gender, Ethnic Origin and Pose of Human Faces IEEE Transactions on Neural Networks, vol. 11, No. 4, Jul. 2000.*

Kwon, Ho Young, et al., Age Classification from Facial Images IEEE, 1994.*

Lyons, Michael J. et al., Automatic Classification of Single Facial Images IEEE Transactions on Pattern Analysis and Machine Intelligence, vol. 21, No. 12, Dec. 1999.*

Shakhnarovich, Gregory et al., A Unified Learning Framework for Real Time Face Detection and Classification International Conference on Automatic Face and Gesture REcognition, IEEE, 2002.*

Rowley, Henry A. et al., Neural Network-Based Face Detection IEEE Transactions on Pattern Analysis and Machine Learning, vol. 20, No. 1, Jan. 1998.*

Farley, John U., et al., A Stochastic Model of Supermarket Traffic Flow Operations Research, vol. 14, No. 4, Jul.-Aug. 1966.*

Lam, Shun Yin, Uncovering the Multiple Impacts of Retail Promotion on Apparel Store Performance—A Study Based on Shopper Count Data, The University of Western Ontario, Dec. 1997.*

Underhill, Paco, Why We Buy—The Science of Shopping Simon & Schuster, 1999.*

Haritaoglu, Smail et al., Attentive Billboards IEEE, 2001.*

ArcView Business Analyst—White Papger ESRI, Inc., Jan. 2000.*

ArcView GIS—product brochure ESRI, Inc., Mar. 2000.*

Daniel, Larry et al., Inside MapInfo Professional—Third Edition OnWord Press, May 18, 2001, ISBN-10: 9780766834729.*

Lash, Albert L, How to Successfully Manage Retail Merchandising and In-Store Advertising Campaigns Savonix Corporation, May 8, 2005.*

Caliper.com Web Pages—Maptitude Overview Caliper, Feb. 1999, Retrieved from Archive.org Nov. 16, 2005.*

I. Haritaoglu, et al., "W4: Real-time surveillance of people and their activities," IEEE Transactions on Pattern Analysis and Machine Intelligence, vol. 22, No. 8.

K. Mikolajczyk, et al., "Human detection based on a probabilistic assembly of robust part detectors," European Conference on Computer Vision, 2004.

K. Ueki, et al., "A method of gender classification by integrating facial, hairstyle, and clothing images," International Conference on Pattern Recognition, 2004.

* cited by examiner

| AREA 1 | TIME | | | | | | 610 |
|---|---|---|---|---|---|---|---|
| | T1 | T2 | T3 | | Tn-1 | Tn | |
| DEMOGRPHIC CATEGORY | CAT.1 | 45% | 47% | 50% | ... | 52% | 56% |
| | CAT.2 | 35% | 28% | 34% | ... | 40% | 42% |
| | CAT.3 | 20% | 25% | 16% | ... | 8% | 2% |

UNIT: %

⋮

| AREA N | TIME | | | | | | 611 |
|---|---|---|---|---|---|---|---|
| | T1 | T2 | T3 | | Tn-1 | Tn | |
| DEMOGRPHIC CATEGORY | CAT.1 | 30% | 32% | 35% | ... | 33% | 30% |
| | CAT.2 | 20% | 28% | 34% | ... | 26% | 22% |
| | CAT.3 | 50% | 40% | 31% | ... | 41% | 48% |

UNIT: %

Fig. 10

METHOD AND SYSTEM FOR CHARACTERIZING PHYSICAL RETAIL SPACES BY DETERMINING THE DEMOGRAPHIC COMPOSITION OF PEOPLE IN THE PHYSICAL RETAIL SPACES UTILIZING VIDEO IMAGE ANALYSIS

CROSS-REFERENCE TO RELATED APPLICATIONS

This application claims the benefit of U.S. Provisional Patent Application No. 60/855,223, filed Oct. 30, 2006.

FEDERALLY SPONSORED RESEARCH

Not Applicable

SEQUENCE LISTING OR PROGRAM

Not Applicable

BACKGROUND OF THE INVENTION

1. Field of the Invention

The present invention is a method and system for characterizing physical space based on automatic demographics measurement, using a plurality of means for capturing images and a plurality of computer vision technologies, such as face detection, person tracking, body parts detection, and demographic classification of the people, on the captured visual information of the people in the physical space.

2. Background of the Invention

Media and Product Match

There have been attempts to customize and distribute matching media content, such as advertising content, to customers based on customer profiles, demographic information, or customer purchase history from the customer in the prior art.

U.S. Pat. No. 6,119,098 of Guyot, et al. (hereinafter Guyot) disclosed a method and apparatus for targeting and distributing advertisements over a distributed network, such as the Internet, to the subscriber's computer. The targeted advertisements were based on a personal profile provided by the subscriber. Guyot was primarily intended for the subscriber with a computer at home, not at a physical space, such as a retail store or a public place, and the targeted advertisement creation relied on the non-automatic response from the customer. U.S. Pat. No. 6,182,050 of Ballard disclosed a method and apparatus for distributing advertisements online using target criteria screening, which also provided a method for maintaining end user privacy. In the disclosure, the demographic information or a desired affinity ranking was gathered by the end user, who completed a demographic questionnaire and ranked various categories of products and services. Like Guyot, Ballard is foreign to the concept of automatically gathering the demographic information from the customers without requiring any cumbersome response from the end user in a physical space, such as a retail store.

U.S. Pat. No. 6,055,573 of Gardenswartz, et al. and its continuation U.S. Pat. No. 6,298,330 of Gardenswartz, et al. (hereinafter Gardenswartz) disclosed a method and apparatus for communicating with a computer in a network based on the offline purchase history of a particular customer. Gardenswartz included the delivery of a promotional incentive for a customer to comply with a particular behavioral pattern. In Gardenswartz, the customer has to supply the registration server with information about the customer, including demographics of the customer, to generate an online profile. Gardenswartz clearly lacks the feature of automatically gathering the demographic information.

U.S. Pat. No. 6,847,969 of Mathai, et al. (hereinafter Mathai) disclosed a method and system for providing personalized advertisements to customers in a public place. In Mathai, the customer inserts a personal system access card into a slot on a terminal, which automatically updates the customer profile based on the customer's usage history. The customer profile is used for targeted advertising in Mathai. However, the usage of a system access card is cumbersome to the customer. The customer has to carry around the card when shopping, and the method and apparatus is not usable if the card is lost or stolen. U.S. Pat. No. 6,529,940 of Humble also disclosed a method and system for interactive in-store marketing, using interactive display terminals that allow customers to input feedback information to the distributed marketing messages.

U.S. Pat. Appl. Pub. No. 2003/0216958 of Register, et al. and its continuation-in-part U.S. Pat. Appl. Pub. No. 2004/0128198 of Register, et al. (hereinafter Register) disclosed a method and system for network-based in-store media broadcasting. Register disclosed each of the client player devices is independently supported by the communication with the internal audio/visual system installed in the business location, and he also disclosed a customizable broadcast is supported on each of the client player devices, specific to the particular business location. However, Register is foreign to the concept of automatically measuring the demographic information of the customers in the particular business location using the computer vision technology as the customization method of the contents for each client player device.

U.S. Pat. Appl. Pub. No. 2006/0036485 of Duni, et al. (hereinafter Duni) disclosed a method and system for presenting personalized information to consumers in a retail environment using the RFID technology. Duri very briefly mentioned the computer vision techniques as a method to locate each customer, but Duri is clearly foreign to the concept of utilizing an image classifier in the computer vision technologies to gather demographic information of the customers to customize the media contents in a media network.

U.S. Pat. No. 7,003,476 of Samra, et al. (hereinafter Samra) disclosed a system and method for targeted marketing using a 'targeting engine', which analyzes data input and generates data output. Samra used historical data to determine a target group based on a plurality of embedded models, where the models are defined as predicted customer profiles based on historic data, and the models are embedded in the 'targeting engine'. In Samra, the 'targeting engine' maintains a customer database based on demographics, but Samra includes income, profession, marital status, or how long at a specific address as the demographic information, which cannot be automatically gathered by any computer vision algorithms over the visual information of the customers. Therefore, Samra is clearly foreign to the idea of measuring the demographic information automatically using computer vision technologies for matching the media contents to the demographics in a media network.

Media and Product Marketing Effectiveness

There have been earlier attempts to measure the media advertising effectiveness in a targeted environment, such as in a media network or in a retail store, and to understand the customers' shopping behavior by gathering various market research data.

U.S. Pat. No. 4,972,504 of Daniel, Jr., et al. (hereinafter Daniel, Jr.) and U.S. Pat. No. 5,315,093 of Stewart disclosed market research systems for sales data collection. U.S. Pat.

No. 5,331,544 of Lu, et al. (hereinafter Lu) disclosed an automated system for collecting market research data. In Lu, a plurality of cooperating establishments are included in a market research test area. Each cooperating establishment is adapted for collecting and storing market research data. A computer system, remotely located from the plurality of cooperating establishments, stores market research data collected from the cooperating establishments. The collected market research data includes monitored retail sales transactions and captured video images of retail customers. The video images of customers are analyzed using a facial recognition system to verify whether the matches to a known gallery of frequent customers are established.

U.S. Pat. Appl. Pub. No. 2006/0041480 of Briggs disclosed a method for determining advertising effectiveness of cross-media campaigns. Briggs' method is to provide media suggestions on each media based on the advertising effectiveness analysis for the cross-media campaigns. Although Briggs disclosed strategic "six basic steps" to assess the advertising effectiveness for multiple media, he is clearly foreign to the concept of actually and automatically measuring the media effectiveness of an individual or a group of viewers based on the visual information from the viewers.

While the above mentioned prior arts tried to deliver matching media contents to the customers or while they tried to measure the media advertising effectiveness in a physical space, they are clearly foreign to the concept of utilizing the characterization information of the physical space, which is based on the automatic and actual measurement of the demographic composition of the people in the physical space. With regard to the media match, the prior arts used non-automatic demographic information collection methods from customers using cumbersome portable monitors, assessment steps, customer profiles, a customer's purchase history, or various other non-automatic devices and tools. In the prior arts, the attempts to measure the media effectiveness also relied on cumbersome requests for feedback from the customers or manual input, such as using questionnaires, registration forms, or electronic devices. Their attempts are clearly lacking the capability of matching the media contents to the characteristics of the physical space based on the automatic and actual demographic composition measurement in the physical space, using the computer vision technology for the demographics, such as gender, age, and ethnicity ratio, without requiring any cumbersome involvement from the customer.

The present invention is a method and system for characterizing a physical space based on automatic demographics measurement, using a plurality of means for capturing images and a plurality of computer vision technologies, such as face detection, person tracking, body parts detection, and demographic classification of the people, on the captured visual information of the people in the physical space, and the present invention is called demographic-based retail space characterization (DBR). It is an objective of the present invention to provide an efficient and robust solution that solves the aforementioned problems in the prior art.

Computer vision algorithms have been shown to be an effective means for detecting and tracking people. These algorithms also have been shown to be effective in analyzing the demographic information of people in the view of the means for capturing images. This allows for the possibility of connecting the visual information, especially the demographic composition of the people, from a scene in a physical space to the characterization of the physical space. The invention automatically and unobtrusively analyzes the customers' demographic information without involving any hassle of feeding the information manually by the customers or operator. Then the invention provides the automatic and actual demographic composition measurement to the decision maker of the physical space to help characterize the physical space as one of the key criteria for the characterization.

Body Detection and Tracking

There have been prior attempts for detecting and tracking human bodies in videos.

The article by I. Haritaoglu, et. al (hereinafter Haritaoglu) "W4: Real-Time Surveillance of People and Their Activities," IEEE Transactions on Pattern Analysis and Machine Intelligence, Vol. 22, No. 8. disclosed a method for detecting and tracking a human body in digital images. The system first learns and models background scenes statistically to detect foreground objects, even when the background is not completely stationary. It then distinguishes people from other objects using shape and periodic motion cues. The system tracks multiple people simultaneously by constructing an appearance model for each person during tracking. It also detects and tracks six main body parts (head, hands, feet, torso) of each person using a static shape model and second order motion tracking of dynamic appearance models. It also determines whether a person is carrying an object, and segments the object so it can be tracked during exchanges.

U.S. Pat. No. 6,421,463 of Poggio, et. al (hereinafter Poggio) disclosed a trainable object detection system and technique for detecting objects such as people in static or video images of cluttered scenes. The system and technique can be used to detect highly non-rigid objects with a high degree of variability in size, shape, color, and texture. The system learns from examples and does not rely on any a priori (hand-crafted) models or on motion. The technique utilizes a wavelet template that defines the shape of an object in terms of a subset of the wavelet coefficients of the image. It is invariant to changes in color and texture and can be used to robustly define a rich and complex class of objects such as people. The invariant properties and computational efficiency of the wavelet template make it an effective tool for object detection.

The article by K. Mikolajczyk, et. al (hereinafter Mikolajczyk) "Human detection based on a probabilistic assembly of robust part detectors," European Conference on Computer Vision 2004, presents a novel method for human detection in single images which can detect full bodies as well as close-up views in the presence of clutter and occlusion. The system models a human body as flexible assemblies of parts, and robust part detection is the key to the approach. The parts are represented by co-occurrences of local features, which capture the spatial layout of the part's appearance. Feature selection and the part detectors are learned from training images using AdaBoost.

The disclosed system utilizes methods similar to the prior arts summarized above. As in Haritaoglu, the motion foreground is segmented to limit the search space of human bodies. A machine learning based approach is used to robustly detect and locate the human figure in images, as in Poggio and Mikolajczyk. However, the disclosed application assumes frontal human body pose; therefore, the method makes use of simpler body appearance model, where the shapes and the spatial arrangement of body parts are encoded using a graphical Bayesian method, such as Bayesian Network or Hidden Markov Model. Once the body image is located, the Bayesian body model adapts to the specific person's bodily appearance, and keeps the identity of the person for the tracking.

Non-Face Based Gender Classification

There have been prior attempts for classifying the gender of a person based on the bodily image signatures other than the face.

The article by K. Ueki, et. al (hereinafter Ueki), "A Method of Gender Classification by Integrating Facial, Hairstyle, and Clothing Images," International Conference on Pattern Recognition 2004, presents a method of gender classification by integrating facial, hairstyle, and clothing images. The system first separates the input image into facial, hair and clothing regions, then independently computed PCAs and GMMs from thousands of sample images are applied to each region. The classification results are then integrated into a single score using some known priors based on the Bayes rule.

The disclosed invention utilizes a more general approach than Ueki for the gender classification, using bodily appearance signature. Instead of using the combination of upper body appearance signature (face, hairstyle, and necktie/décolleté) in grey scale for gender classification, the disclosed method utilizes the combination of more comprehensive bodily appearance signature (shape of the hair region, the body figure, and the color composition of the clothing). The bodily appearance signature is extracted using the Bayesian appearance model, according to the information provided by the body detection/tracking stage. The appearance signature is trained on thousands of images, each annotated with gender label. The trained classification machine serves as a stand-alone classifier when the customer's facial image is not available. The body-based classification can only apply to the gender classification.

Face Based Demographics Classification

There have been prior attempts for recognizing the demographic category of a person by processing the facial image using a machine learning approach.

U.S. Pat. No. 6,990,217 of Moghaddam, et al. (hereinafter Moghaddam) disclosed a method to employ Support Vector Machine to classify images of faces according to gender, by training the images including images of male and female faces; determining a plurality of support vectors from the training images for identifying a hyperplane for the gender decision; and reducing the resolution of the training images and the test image by sub-sampling before supplying the images to the Support Vector Machine.

U.S. Pat. Appl. Pub. No. 20030110038 of Sharma, et al. (hereinafter Sharma) disclosed a computer software system for multi-modal human gender classification, comprising: a first-mode classifier classifying first-mode data pertaining to male and female subjects according to gender and rendering a first-mode gender-decision for each male and female subject; a second-mode classifier classifying second-mode data pertaining to male and female subjects according to gender and rendering a second-mode gender-decision for each male and female subject; and a fusion classifier integrating the individual gender decisions obtained from said first-mode classifier and said second-mode classifier and outputting a joint gender decision for each of said male and female subjects.

The either prior arts (Moghaddam and Sharma) for demographics classification mentioned above aim to classify a certain class of demographics profile (only gender) based on the image signature of faces. These approaches deal with a much smaller scope of problems than the claimed method tries to solve; they both assume that the facial regions are identified and only address the problem of individual face classification. They don't address the problem of detecting and tracking the faces for determining the demographic identity of a person over the course of his/her facial exposure to the imaging device.

The proposed invention is a much more comprehensive solution where the automated system captures video frames, detects customers in the frames, tracks the people individually, corrects the pose of the faces, and finally classifies the demographics profiles of the customers—both of the gender and the ethnicity. The dedicated facial geometry correction step improves the face classification accuracy.

The present invention utilizes the motion foreground segmentation to locate the region where the customers entering a specified region can be detected. The method makes use of a frontal body appearance model, where the shapes and the spatial arrangement of body parts are encoded using a graphical Bayesian method. Once the body image is located, the Bayesian body model adapts to the specific person's bodily appearance, and keeps the identity of the person for the tracking. The estimated footfall location of the person determines whether the person has entered the monitored area. If the frontal facial image is available, then the learning machine based face classifier is utilized to determine the demographics group of the person. If the frontal facial image is not available, then the demographics classifier utilizes the holistic bodily appearance signature as a mean to distinguish between male and female.

SUMMARY

The present invention is a method and system for characterizing physical space based on automatic demographics measurement, using a plurality of means for capturing images and a plurality of computer vision technologies.

Although the disclosed method is described in the context of retail space, the present invention can be applied to any physical space that has a restricted boundary. In the present invention, the physical space characterization can comprise various types of characterization depending on the objective of the physical space.

It is one of the objectives of the present invention to provide the automatic demographic composition measurement to facilitate the physical space characterization.

Overview

The present invention provides a solution to characterize a retail location or portion of a retail location based on the demographic makeup of shoppers in the store or part of the store. The solution is based on proprietary technology and processes that automatically measure the demographic composition of shoppers and characterize a particular store, department, aisle or category based on this composition.

The characterization provided by the present invention allows retailers to better plan and track the progress of their efforts in multiple functional areas, including marketing and merchandising. Having an understanding of characterizations of a particular store or area within a store enables extremely accurate targeting, or micro-marketing, to specific demographic groups.

Micro-marketing involves targeted efforts for a specific, narrow group of consumers or shoppers. It is an extension of customer-centric strategies that aim to better serve the customers as a whole by addressing individual segments separately and with particular tactics. Characterizing specific stores or subsections within stores provides data critical for customer-centricity and micro-marketing initiatives.

Out-of-Store Marketing and Promotions

Retailers can utilize the characterization of retail locations to measure the effectiveness of out-of-store media in driving a targeted demographic group to the stores. This measurement can also be used to fine tune content/messaging and the media mix with respect to which media channels are best for targeting specific customers. Such feedback about the impact of various out-of-store efforts can be leveraged in the planning process for out-of-store media to achieve corporate goals while ensuring the highest region of interest (ROI) on these marketing dollars.

In-Store Marketing and Merchandising

Just as understanding the characterization of stores as a whole is important to gauging out-of-store marketing and promotional efforts, characterizations of subsections of a store are highly valuable in determining how in-store marketing dollars are spent. A trend is emerging in retail whereby the merchandising of products is being driven by characterization of a particular store or market. This translates to different in-store signage, POP displays and other visual merchandising aspects relative to the composition of shoppers.

Product Assortment, Allocation and Placement

Retailers can utilize store characterization data to better match the products they carry to the shoppers that frequent their stores. By understanding the demographic makeup of the shoppers of a particular location, key decisions can be made regarding which products are stocked, how much shelf space is devoted to particular products, and where the products are placed within the store. This accurate matching based on statistical characterization data results not only in improved customer satisfaction, but also in more efficient ordering and inventory management.

Media Effectiveness Measurement and Verification

It is another objective of the present invention to measure media effectiveness based on the demographics. Utilizing this capability, the information that drives customers to buy a certain category of products, or how the subtle changes in merchandise location, offering, media affects the demographic composition, can be known. Therefore, based on the media effectiveness measurement by the present invention, the media mix, in-store and off-store media, such as TV, radio, prints, inserts, fixture, or Internet advertisement, can be strategically changed.

It is therefore a further objective of the present invention to enable actual verification of demographic composition in a physical space, such as in a retail space, by actually measuring the demographic composition for those who actually visited the retail space, whose result may not be the same as that of the census data in the region where the retail space is located. In an embodiment of the present invention, the DBR can precisely provide the actual count per demographic group in the physical space.

It is a further objective of the present invention to measure the pattern of changes in demographics due to the changes in the matching advertisement.

It is a further objective of the present invention to help in different servicing strategies, so that the application of the present invention can attract a specific demographic group, based on the actually measured demographic data, by matching the needs for the particular group.

The demographic classification and composition measurement of people in the physical space is performed automatically based on a novel usage of a plurality of means for capturing images and a plurality of computer vision technologies on the captured visual information of the people in the physical space. The plurality of computer vision technologies can comprise face detection, person tracking, body parts detection, and demographic classification of the people, on the captured visual information of the people in the physical space.

DRAWINGS

Figures

FIG. 10 shows exemplary statistics of the demographic information for each target measurement area.

DETAILED DESCRIPTION OF THE INVENTION

Figure 1:
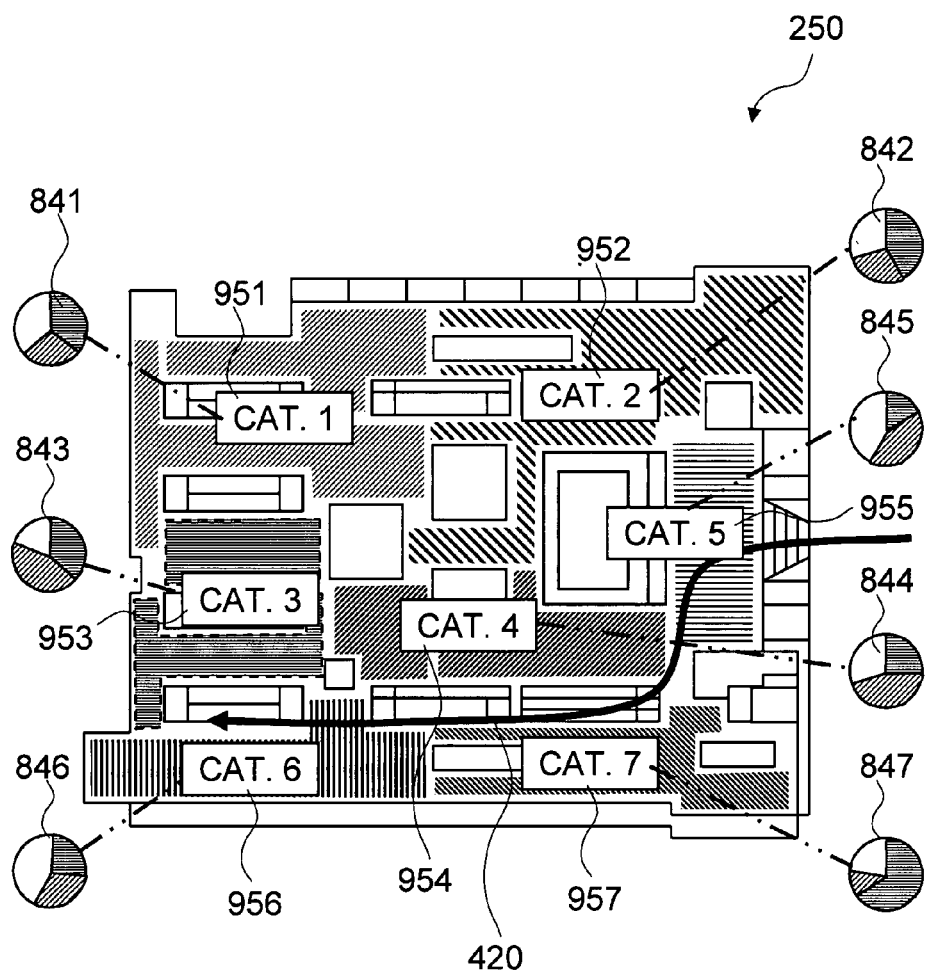
FIG. 1 shows an exemplary embodiment of physical space characterization based on the demographic composition measurement by the present invention.

FIG. 1 shows an exemplary embodiment of "physical space characterization" 250 based on the demographic composition measurement by the present invention. The present invention is a method and system for characterizing physical space based on automatic demographics measurement, using a plurality of means for capturing images and a plurality of computer vision technologies. The present invention is called demographic-based retail space characterization (DBR). Although the disclosed method may be described in the context of retail space depending on the exemplary embodiments in this specification of the invention, the present invention can be applied to any physical space that has a restricted boundary.

As said, a retail space can be an exemplary physical space, so the DBR can provide a solution to characterize a retail location or portion of a retail location based on the demographic makeup of shoppers in the store or part of the store. The solution is based on proprietary technology and processes that automatically measure the demographic composition of shoppers and characterize a particular store, department, aisle or category based on this composition.

The characterization provided by the present invention allows retailers to better plan and track the progress of their efforts in multiple functional areas, including marketing and merchandising. Having an understanding of characterizations of a particular store or area within a store enables extremely accurate targeting, or micro-marketing, to specific demographic groups.

Micro-marketing involves targeted efforts for a specific, narrow group of consumers or shoppers. It is an extension of customer-centric strategies that aims to better serve the customers as a whole by addressing individual segments separately and with particular tactics. Characterizing specific stores or subsections within stores provides data critical for customer-centricity and micro-marketing initiatives.

In the present invention, the exemplary physical space characterization comprises any characterization that is based on the DBR's automatic and actual demographics measurement data. Therefore, exemplary physical space characterization can comprise a characterization of demographic composition in the physical space, a characterization of product match or media match for the physical space based on the demographic composition, a characterization of the physical space according to the media effectiveness measurement based on the demographic composition measurement, or any characterization of the physical space based on the information calculated by the demographic composition measurement in the physical space. In the case of the characterization of demographic composition in the physical space, the automatic demographic composition measurement by the DBR itself can be used as the automatic characterization of the physical space.

The demographic classification and composition measurement of people in the physical space is performed automatically based on a novel usage of a plurality of means for capturing images and a plurality of computer vision technologies on the captured visual information of the people in the physical space. The plurality of computer vision technologies can comprise face detection, person tracking, body parts detection, and demographic classification of the people, on the captured visual information of the people in the physical space.

The DBR can provide the measurement of demographic composition for each predefined area or category.

In an exemplary embodiment of the invention as shown in FIG. 1, the DBR can provide the measurement of demographic composition, such as "Demographic Composition 1" 841, "Demographic Composition 2" 842, "Demographic Composition 3" 843, "Demographic Composition 4" 844, "Demographic Composition 5" 845, "Demographic Composition 6" 846, and "Demographic Composition 7" 847, for each category, "Category 1" 951, "Category 2" 952, "Category 3" 953, "Category 4" 954, "Category 5" 955, "Category 6" 956, and "Category 7" 957, respectively.

Category is a logically defined entity with a group of products, a group of product types, space, areas in a store, display of a group of products, or department with similar relevance in the present invention. The decision maker in the physical space can characterize the physical space based on the demographic composition information in each category.

As said, predefined area in the physical space can be an exemplary category. When the DBR provides the measurement of demographic composition for each predefined area in the physical space, the decision maker of the entire physical space can characterize each predefined area based on the demographic composition information for each predefined area.

The decision maker can also characterize the entire physical space based on the characterization for each predefined area in the physical space, such as the aggregated data of all the characterization for each predefined area. Whether to characterize the physical space globally or locally is up to the objective of the decision maker in using the DBR system.

Figure 2:
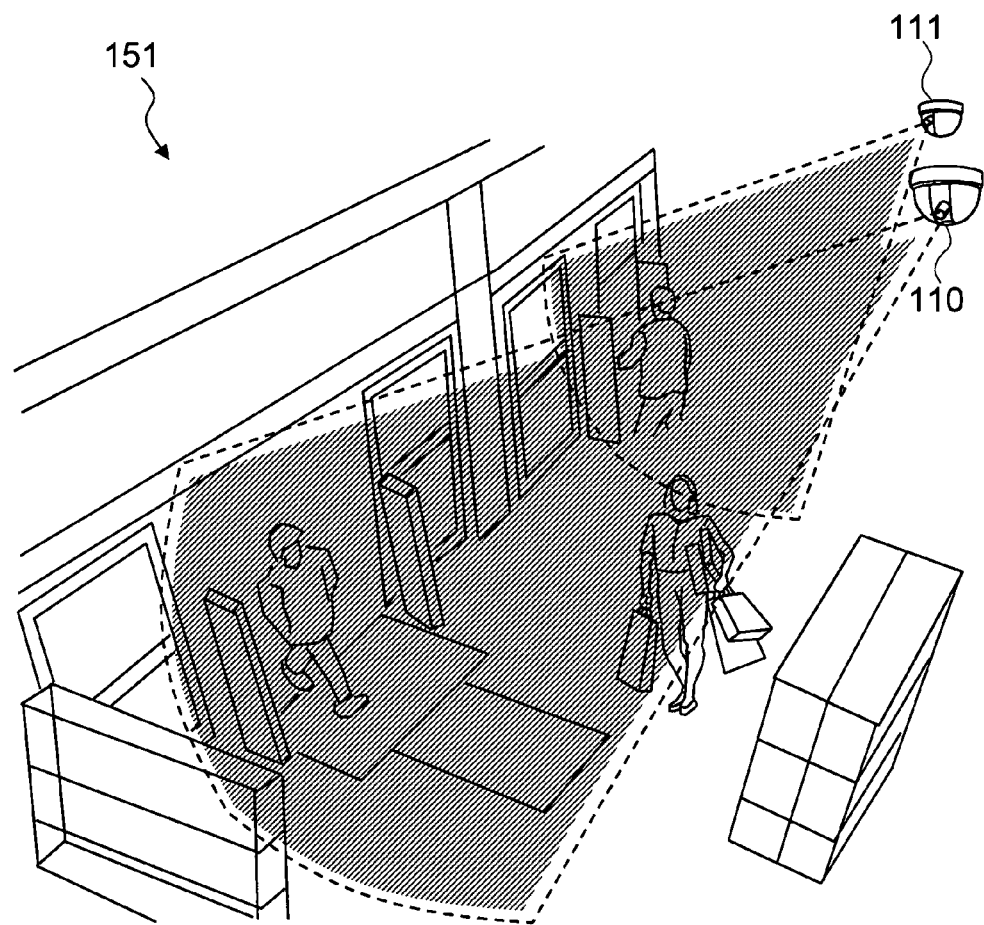
FIG. 2 shows an overview of an exemplary embodiment of the present invention when the means for capturing images are placed at the entrance/exit area of the physical space.

FIG. 2 shows an overview of an exemplary embodiment of the present invention when the means for capturing images are placed at the entrance/exit area of the physical space. In the exemplary embodiment shown in FIG. 2, the plurality of means for capturing images, such as the exemplary "means for capturing images 1" 110 and the exemplary "means for capturing images 2" 111, measures the demographic data of the people at the "entrance and exit" 151 of a physical space.

Aggregated measurement of the demographic composition at all the entrances and exits of a physical space can provide an easy and simple solution for characterizing the entire store.

Figure 3:
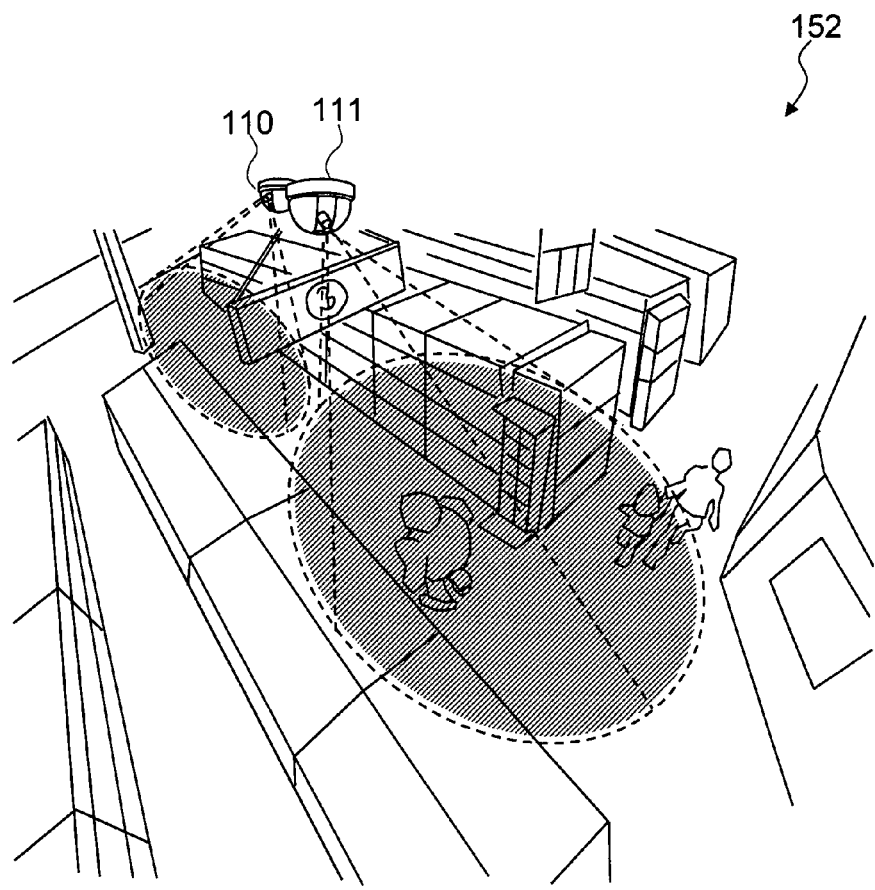
FIG. 3 shows an overview of an exemplary embodiment of the present invention when the means for capturing images are placed at the aisle area of the physical space.

FIG. 3 shows an overview of an exemplary embodiment of the present invention when the means for capturing images are placed at the aisle area of the physical space. In the exemplary embodiment shown in FIG. 3, the plurality of means for capturing images, such as the exemplary "means for capturing images 1" 110 and the exemplary "means for capturing images 2" 111, measures the demographic data of the people at the aisle area 152 of a physical space.

The demographic composition measurement at the aisle area provides information for finer level of interest of the demographics for particular products at the specific aisle area.

Figure 4:
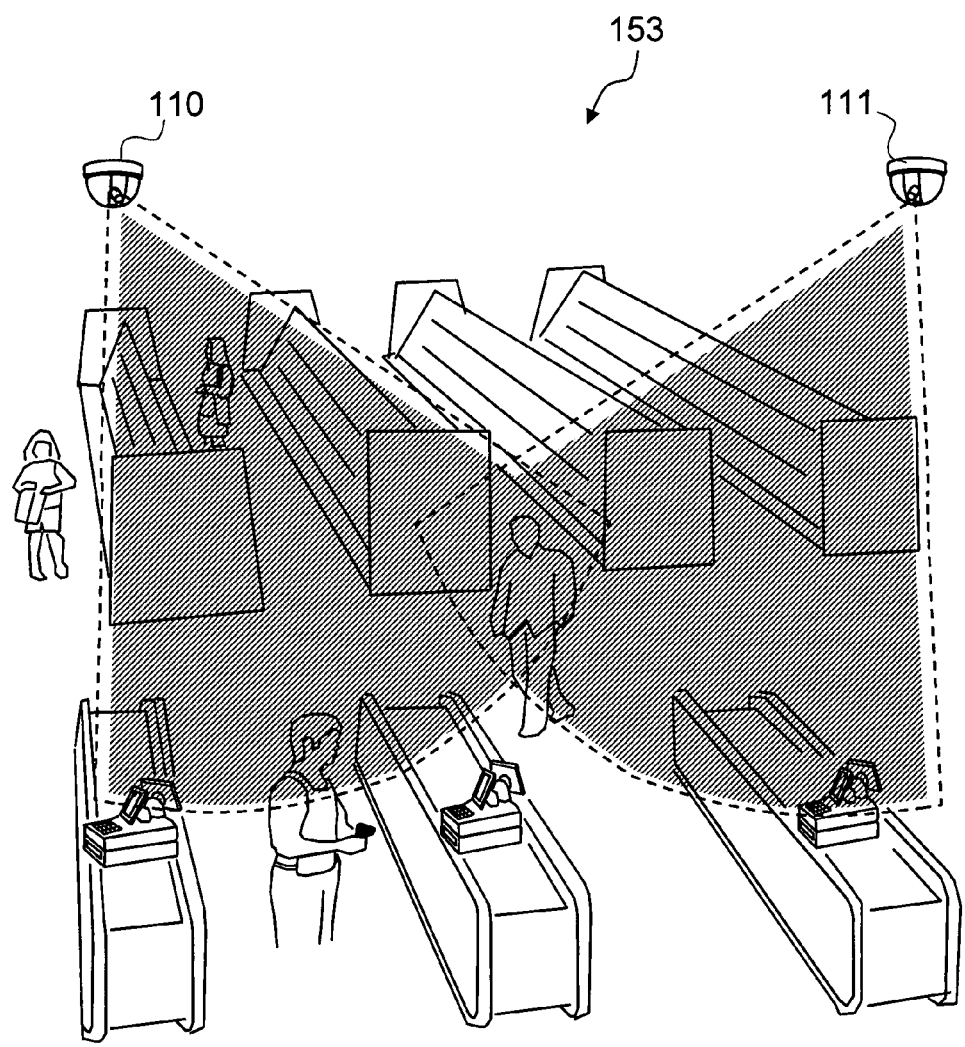
FIG. 4 shows an overview of an exemplary embodiment of the present invention when the means for capturing images are placed at the entry point area of the physical space.

FIG. 4 shows an overview of an exemplary embodiment of the present invention when the means for capturing images are placed at the entry point area of the physical space. In the exemplary embodiment shown in FIG. 4, the plurality of means for capturing images, such as the exemplary "means for capturing images 1" 110 and the exemplary "means for capturing images 2" 111, measures the demographic data of the people at the entry point area 153 the physical space. In this exemplary embodiment, the DBR can cover the entry point area where the people's traffic exists, although the area may not be the hot spot in the physical space.

Figure 5:
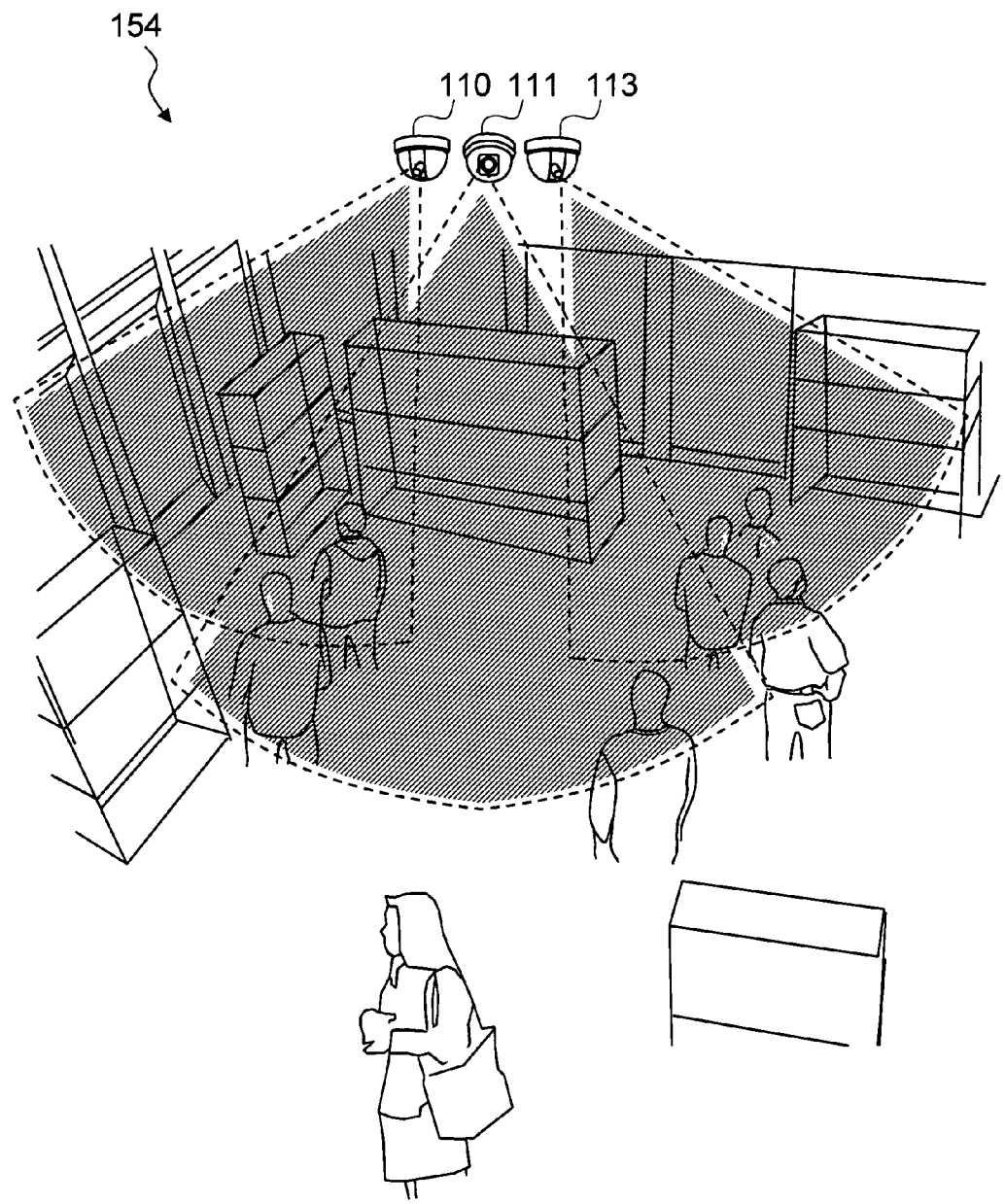
FIG. 5 shows an overview of an exemplary embodiment of the present invention when a plurality of means for capturing images are placed at a predefined open space in the physical space.

FIG. 5 shows an overview of an exemplary embodiment of the present invention when a plurality of means for capturing images are placed at a predefined open space in the physical space. In the exemplary embodiment shown in FIG. 5, the plurality of means for capturing images, such as the exemplary "means for capturing images 1" 110, the exemplary "means for capturing images 2" 111, and the exemplary "means for capturing images N" 113, measures the demographic data of the people at the predefined open space 154 in a physical space. The predefined open space can be defined by the decision maker who tries to characterize a particular hot spot in the physical space.

In the exemplary embodiment shown in FIG. 5, the precise number of the plurality of means for capturing images can vary depending on the size of the predefined open space and the viewing area and install location of each of the plurality of means for capturing images.

Figure 6:
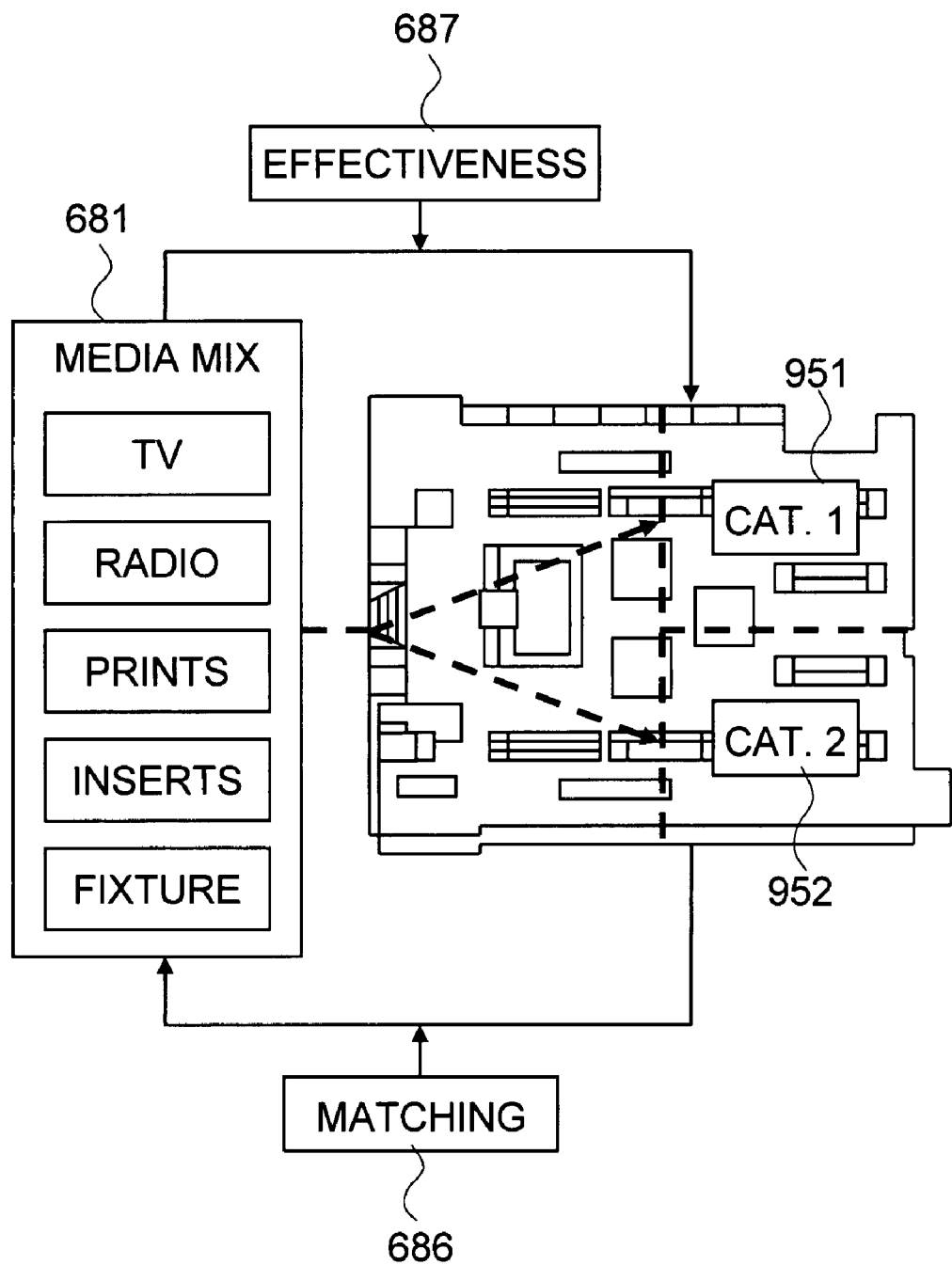
FIG. 6 shows exemplary product match and media effectiveness measurement based on demographic characterization by the present invention.

FIG. 6 shows exemplary product match and media effectiveness measurement based on demographic characterization by the present invention.

Out-of-Store Marketing and Promotions

Retailers can utilize the characterization of retail locations to measure the effectiveness of out-of-store media in driving a targeted demographic group to the stores. This measurement can also be used to fine tune content/messaging and the media mix with respect to which media channels are best for targeting specific customers. Such feedback about the impact of various out-of-store efforts can be leveraged in the planning process for out-of-store media to achieve corporate goals while ensuring the highest region of interest (ROI) on these marketing dollars.

In-Store Marketing and Merchandising

Just as understanding the characterization of stores as a whole is important to gauging out-of-store marketing and promotional efforts, characterizations of subsections of a store are highly valuable in determining how in-store marketing dollars are spent. A trend is emerging in retail whereby the merchandising of products is being driven by characterization of a particular store or market. This translates to different in-store signage, POP displays and other visual merchandising aspects relative to the composition of shoppers.

Product Assortment, Allocation and Placement

Retailers can utilize store characterization data to better match the products they carry to the shoppers that frequent their stores. By understanding the demographic makeup of the shoppers of a particular location, key decisions can be made regarding which products are stocked, how much shelf space is devoted to particular products, and where the products are placed within the store. This accurate matching based on statistical characterization data results not only in improved customer satisfaction, but also in more efficient ordering and inventory management.

As shown in the exemplary embodiment in FIG. 6, one of the capabilities of the present invention is to provide information, which can be used to match 686 demographic characterization to products installed in a physical space. This kind of product assortment based on the demographic composition measurement by the present invention helps to avoid mismatch between customers and products/service/marketing.

Media Effectiveness Measurement and Verification

A capability of the present invention is to measure media effectiveness 687, for both "media effectiveness measurement for the out-of-store marketing and promotions" and "local level media effectiveness measurement for in-store marketing and merchandising", based on the demographics. Utilizing this capability, the information that drives customers to buy a certain category of products or how the subtle changes in merchandise location, offering, media affect the demographic composition, can be known. Therefore, based on the media effectiveness measurement by the present invention 687, the media mix 681, in-store and off-store media, such as TV, radio, prints, inserts, fixture, or Internet advertisement, can be strategically changed.

The present invention enables actual verification of demographic composition in a physical space, such as in a retail space, by actually measuring the demographic composition for those who actually visited the retail space, whose result may not be the same as that of the census data in the region where the retail space is located. In an embodiment of the present invention, the DBR can precisely provide the actual count per demographic group in the physical space. The present invention can also measure the pattern of changes in demographics.

Furthermore, the DBR helps in different servicing strategies, so that the application of the DBR can attract a specific demographic group, based on the actually measured demographic data, by matching the needs for the particular group. The overall advantages of the DBR system and its application can be found in its characteristics of actual measurement, automatic measurement, scalability, and timely process.

Figure 7:
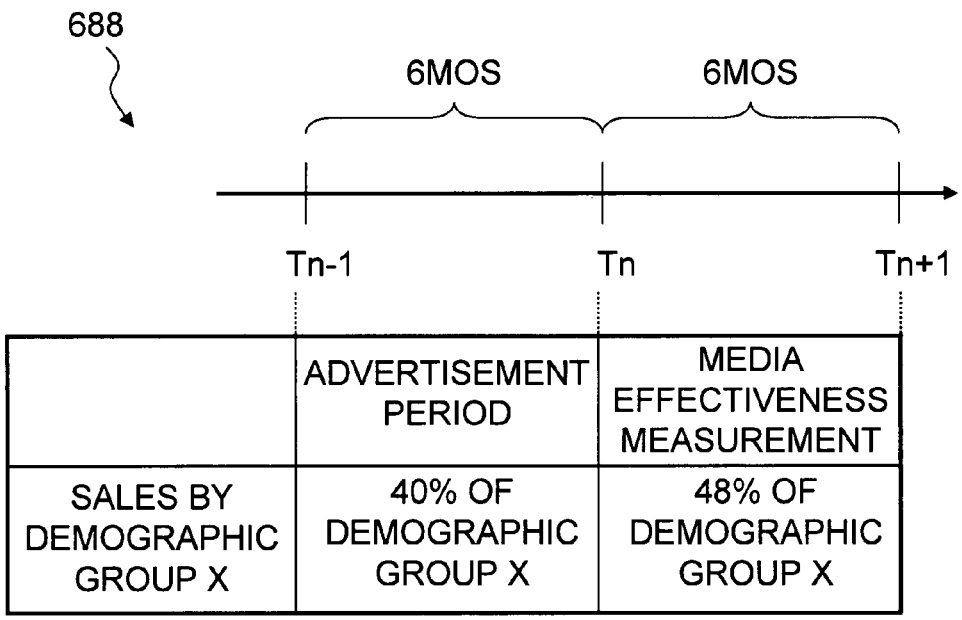
FIG. 7 shows details of an exemplary media effectiveness measurement based on demographic characterization by the present invention.
Figure 7:
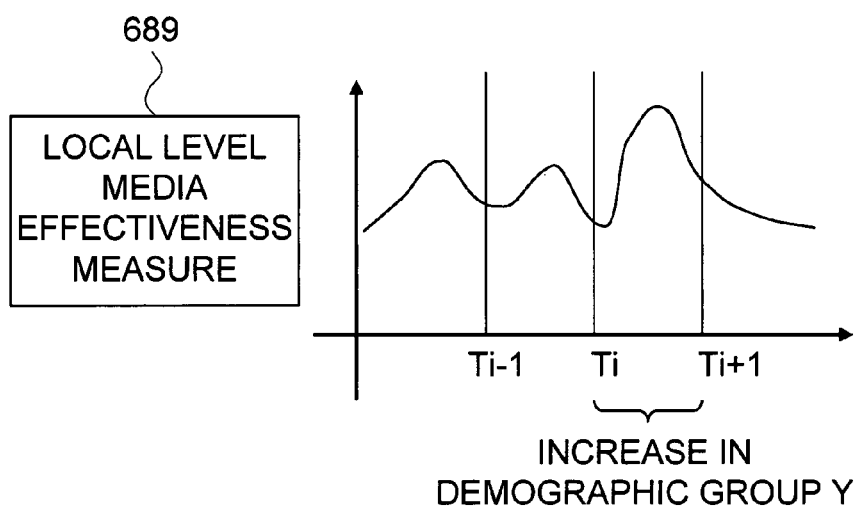

FIG. 7 shows details of an exemplary media effectiveness measurement based on demographic characterization by the present invention.

As shown in the exemplary embodiment in FIG. 7, the DBR can process the "media effectiveness measurement for the out-of-store marketing and promotions" 688 during the period from Tn to Tn+1 after a predefined advertisement period from Tn−1 to Tn. If the percentage of certain demographic group X increase by a certain number, the DBR can automatically detect the increase and change of the demographic composition, and then reflects the increase and change of the demographic composition in the final report. As said, retailers can utilize the information to characterize the retail locations to reflect the measurement, and the characterization can be used to drive a targeted demographic group to the stores.

As shown in the exemplary embodiment in FIG. 7, the DBR can also process the "local level media effectiveness measurement for in-store marketing and merchandising" 689. In the exemplary embodiment of the measurement, an increase in demographic group Y during the period from Ti to Ti+1 can be measured and used for the characterization of subsections in a physical space. As discussed above, characterizations of subsections of a store are highly valuable in determining how in-store marketing dollars are spent, and a trend is emerging in retail whereby the merchandising of products is being driven by characterization of a particular store or market, relative to the composition of shoppers.

Figure 8:
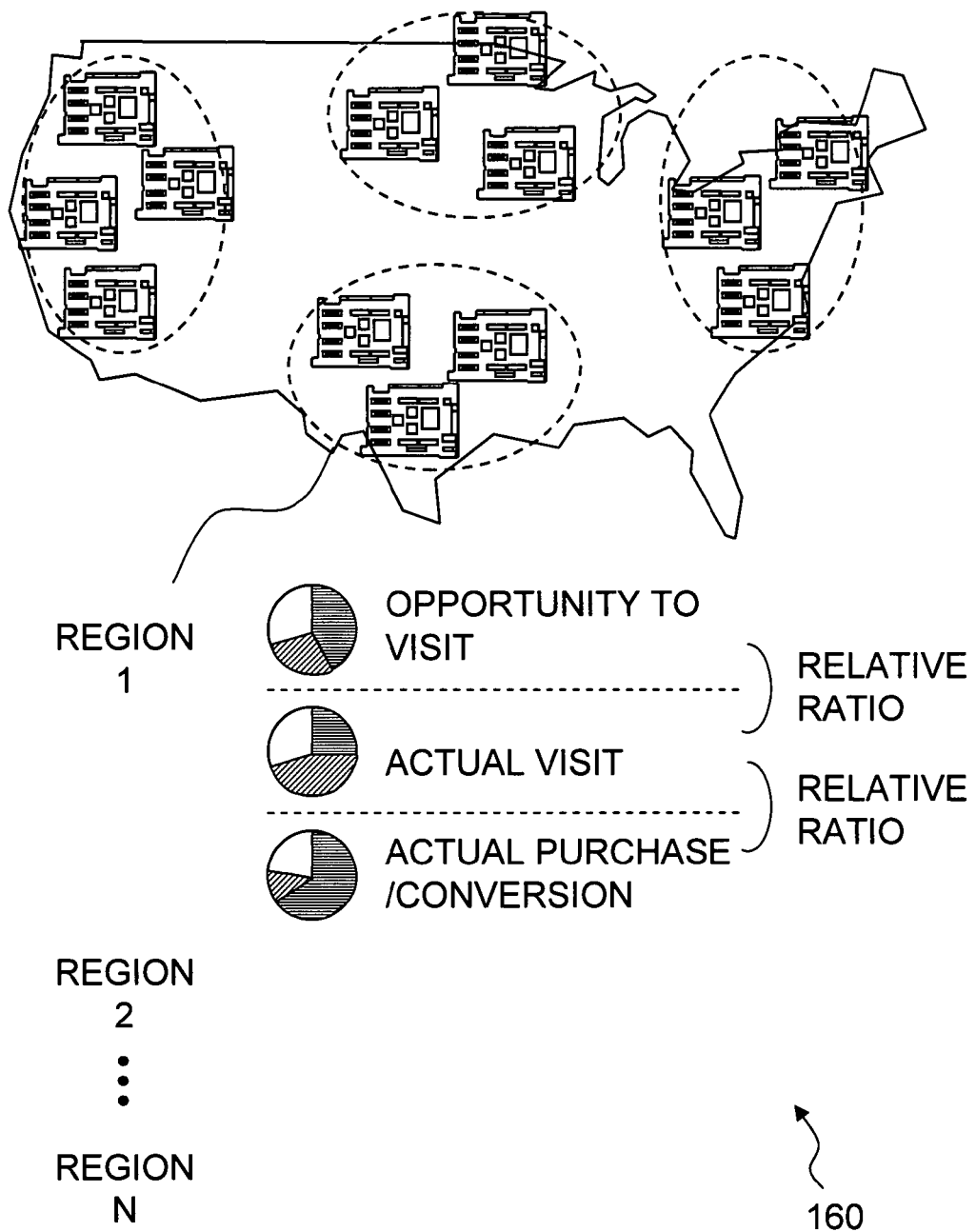
FIG. 8 shows exemplary embodiment of the network of the present invention.

FIG. 8 shows exemplary embodiment of the network of the present invention. The present invention enables actual verification of demographic composition in a physical space, such as in a retail space, by actually measuring the demographic composition for those who actually visited the retail space, whose result may not be the same as that of the census data in the region where the retail space is located. For example, the largest demographic group in the census data for those who have the opportunity to visit may not be the same as the largest demographic group in the actual demographic measurement for those who actually visited the physical space.

In the exemplary embodiment shown in FIG. 8, the DBR can measure the relative ratio between the demographic composition of people who have the opportunity to visit and the demographic composition of people who actually visited the physical space, and the relative ratio between the demographic composition of people who actually visited the physical space and the demographic composition of people who made the actual purchase/conversion, for each of the regions, from the region 1 to the region N, in the network.

Figure 9:
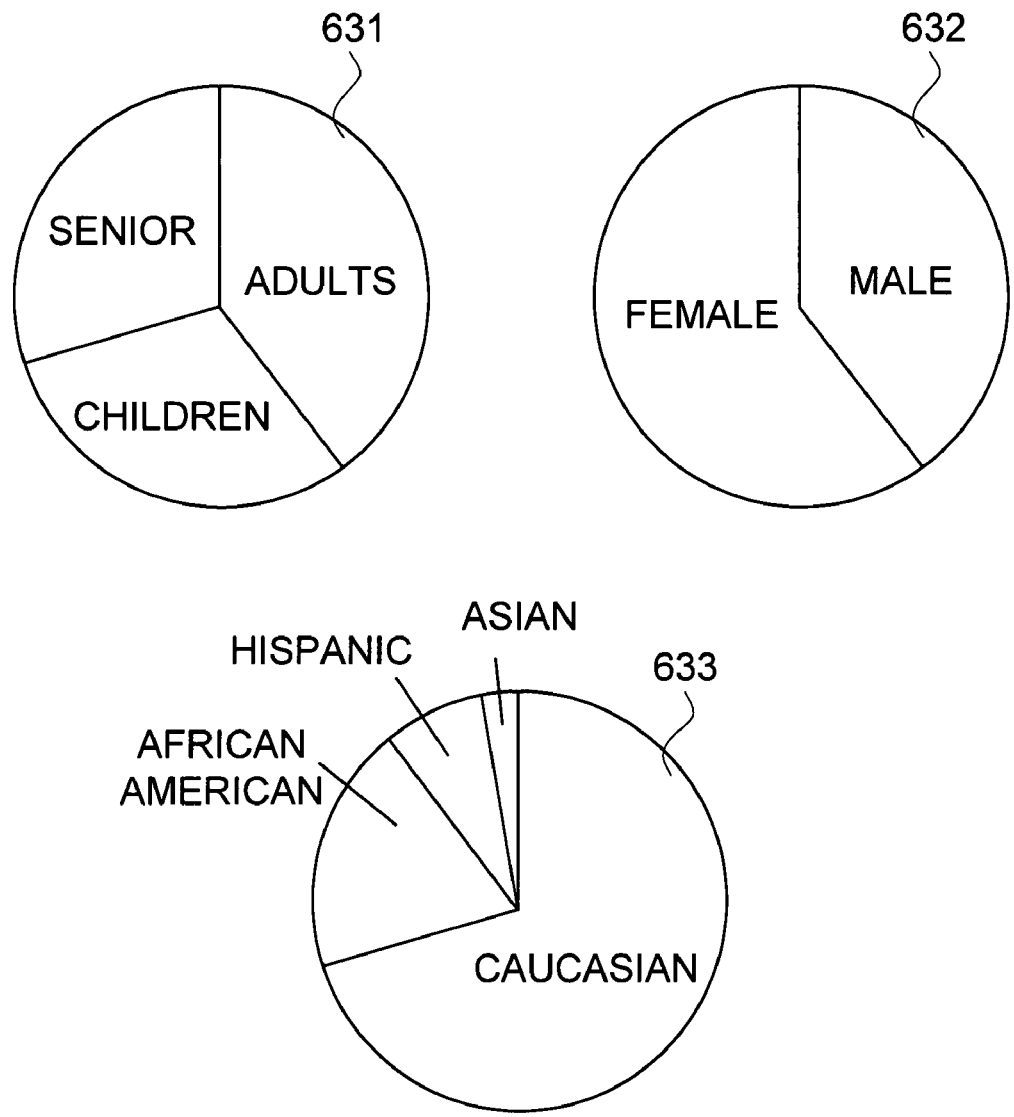
FIG. 9 shows exemplary pie charts of the exemplary demographic information measurement from a means for capturing images, where the pie charts provide useful information to the decision maker for the characterization of the physical space.

FIG. 9 shows exemplary pie charts of the exemplary demographic information measurement from a means for capturing images for an area, where the pie charts provide useful information to the decision maker for the characterization of the physical space based on the demographic composition measurement and information from it. In FIG. 9, an exemplary 'pie chart for age classification' 631, an exemplary 'pie chart for gender' 632, and an exemplary 'pie chart for ethnicity' 633 are shown. The DBR enables the decision maker in the area to characterize the space using the demographic composition information, which is processed based on the actual measurement for the customers' demographics.

FIG. 10 shows exemplary statistics of the demographic information for each target measurement area in a physical space. In the exemplary embodiment, as shown in the exemplary "Table of Demographic Composition for Area A" 610 and "Table of Demographic Composition for Area N" 611, the characterizations can be provided for a given window of time, such as from Tn−1 to Tn, based on the statistical measurement for the demographic composition, and the DBR details an area's audience demographics for that time increment. Each window of time, such as from Tn−1 to Tn, and the entire duration of the measurement period from T1 to Tn, can be decided based on various business goals and level of desired information composition in the physical space.

Figure 11:
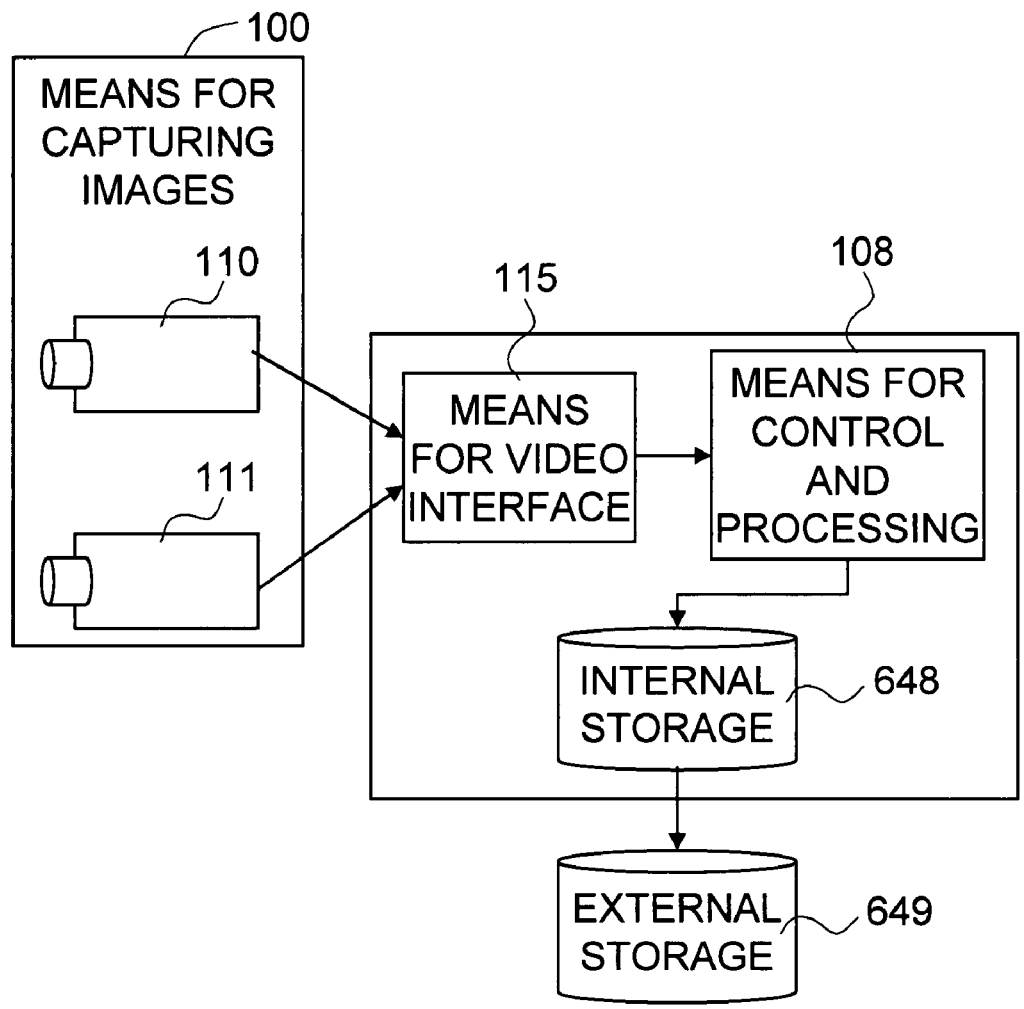
FIG. 11 shows exemplary hardware components in an exemplary embodiment of the present invention.

FIG. 11 shows exemplary hardware components in an exemplary embodiment of the present invention. In an exemplary embodiment of the present invention, the means for capturing images 100 can be connected to the means for video interface 115. In an exemplary embodiment shown in FIG. 11, the plurality of means for capturing images 100, such as the "means for capturing images 1" 110 and the "means for capturing images 2" 111, are connected to the means for video interface 115. The means for control and processing 108 takes digitized video data from the means for video interface 115. The means for control and processing 108 can have "internal means for storing data" 648 or "external means for storing data" 649.

The means for capturing images 100 can be installed near the measured area in a physical space, and they are connected to the means for video interface 115 through cables. Various embodiments of the positioning of the means for capturing images will be discussed later in regards to FIG. 12 through FIG. 14. The means for capturing images 100 can comprise an analog camera, USB camera, or Firewire camera. The means for video interface 115, which can comprise a video frame grabber, USB interface, or Firewire interface, are typically included in the same enclosure as the means for control and processing 108. The means for control and processing 108 can be a general-purpose personal computer, such as a Pentium 4 PC, or a dedicated hardware that can carry out the required computation. The means for control and processing 108, as well as the means for video interface 115, can be placed locally or remotely, as long as the connection to the means for capturing images 100 can be established. The internal means for storing data 648, such as internal hard disks, is placed within the same enclosure as the means for control and processing 108. The external means for storing data 649, such as a network storage driver or internal hard disks contained in a remote computer, can be placed locally or remotely, as long as a means for transferring data is available.

In an exemplary embodiment, a general-purpose USB webcam can serve as the means for capturing images 100. A Pentium 4 2.8 GHz PC having 1 GB memory can serve as a means for control and processing 108, where a generic USB interface included in the PC's motherboard can serve as a means for video interface 115. A generic IDE hard disk drive can serve as the internal means for storing data 648 or the external means for storing data 649.

Figure 12:
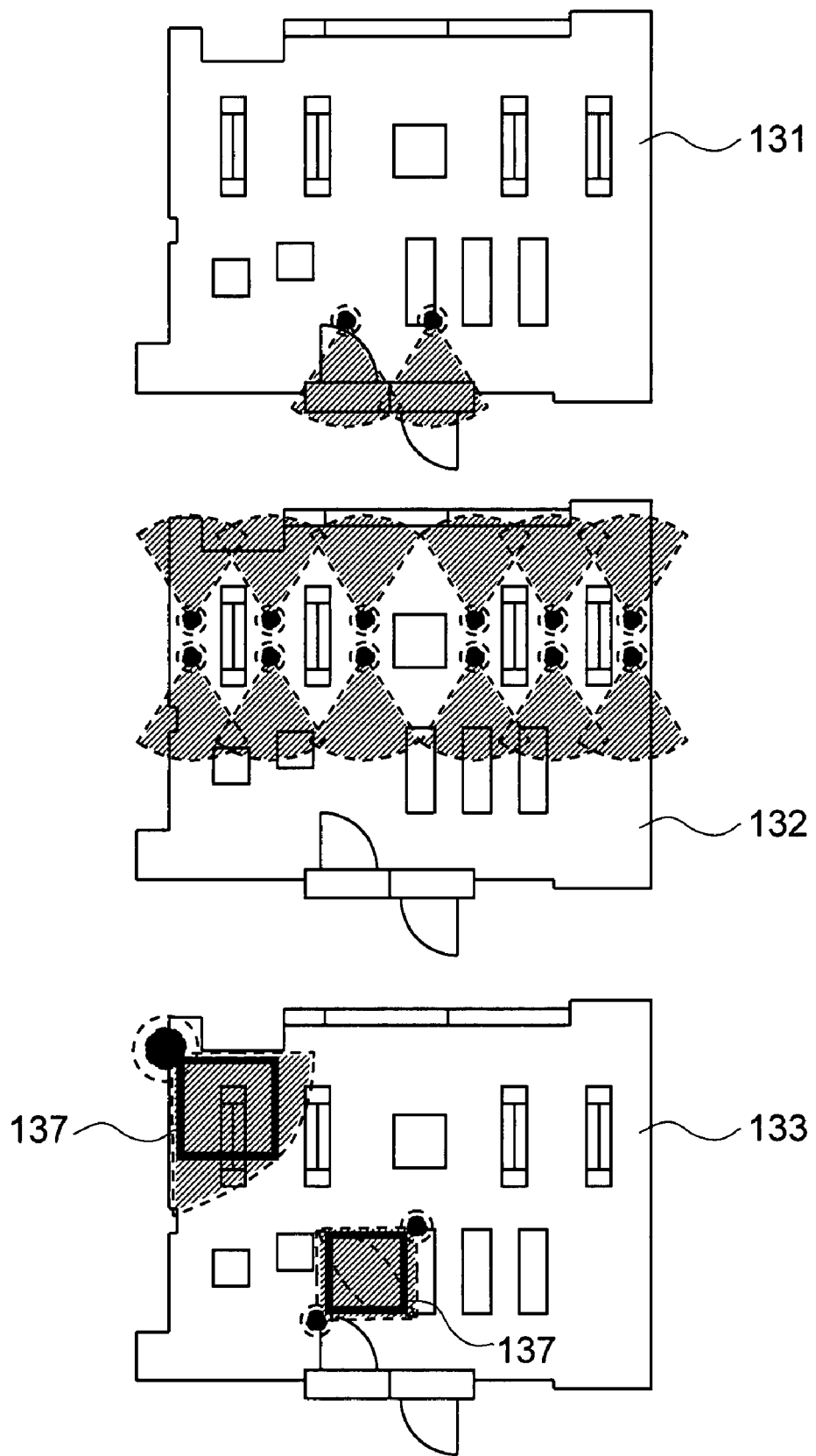
FIG. 12 shows exemplary positioning of a plurality of means for capturing images depending on each target measurement area.
Figure 13:
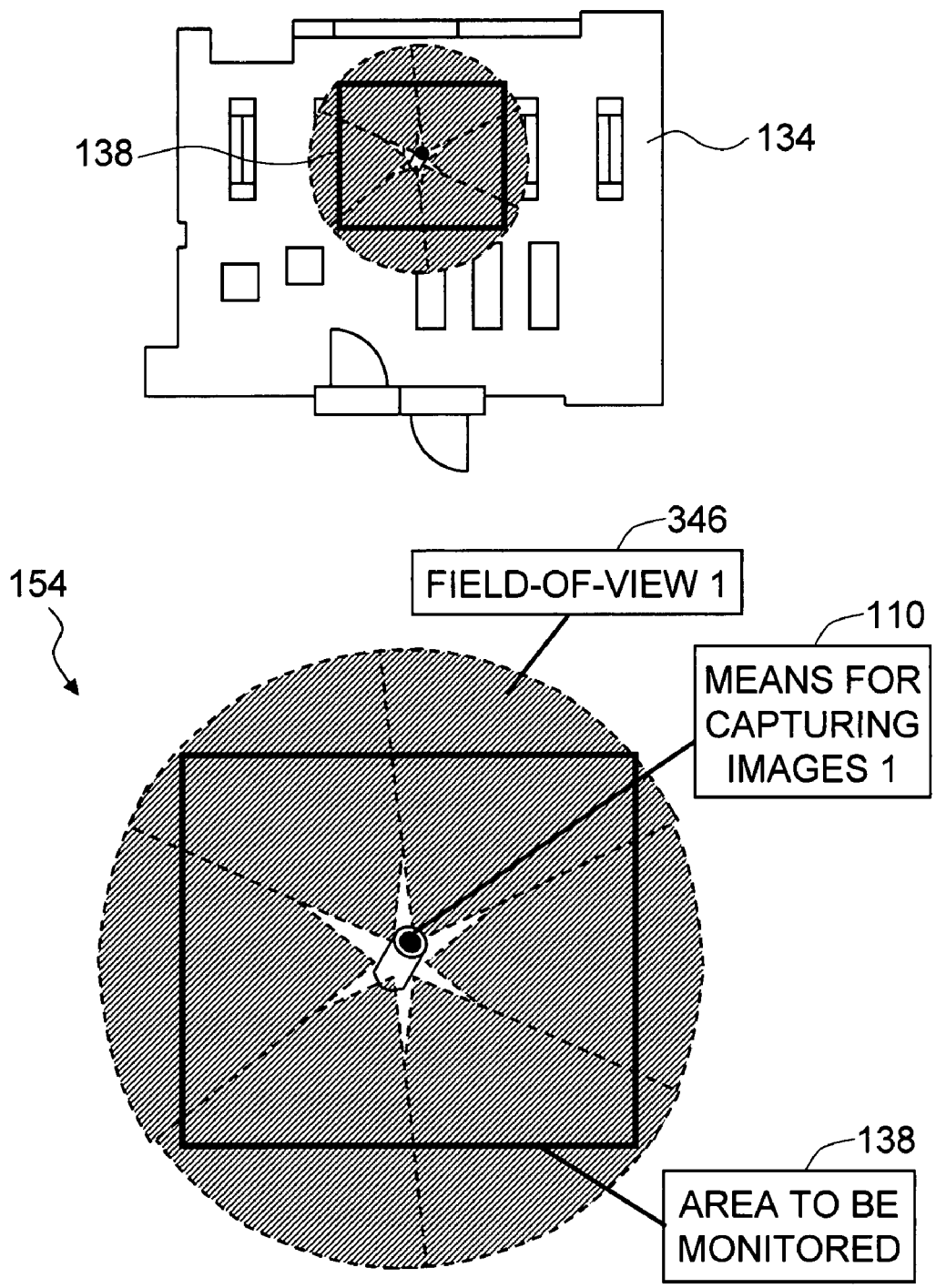
FIG. 13 shows exemplary positioning and set up of a plurality of means for capturing images for the target measurement area of a predefined open space in a physical space.

FIG. 12 shows exemplary positioning of a plurality of means for capturing images depending on each target measurement area. FIG. 13 shows exemplary positioning and setup of a plurality of means for capturing images for the target measurement area of a predefined open space in a physical space.

Placement of the Means for Capturing Images and the Delimitation of the Space

General-purpose color video cameras can be used as the means for capturing images 100 to deliver video frames to the computer via analog, USB, or IEEE1394 connection. A wide-angle lens is preferred to capture as many instances of people as possible, to the extent that the lens also covers the desired range (distance) in view.

There are multiple ways to place the means for capturing images 100, i.e. camera(s), depending on the kind of physical space that needs to be characterized. The desired spatial coverage determines the number of cameras and the focal length of the lens. The height of the camera should be determined to capture the frontal face of people entering the area, and to accurately estimate the footfall positions of the people. The number and the placement of the cameras depend on the kind of space to be monitored:

1. Entrance/Exit Area: In the exemplary embodiment of the "Physical Space Layout with Camera Positioning at Entrance/Exit Area" 131 shown in FIG. 12, the camera is placed inside the store, facing the entrance/exit. The focal length of the lens should be determined to cover the width of the entrance/exit within its field of view. Multiple cameras can be used to cover a wide entrance or multiple entrances.

2. Aisle Area: In the exemplary embodiment of the "Physical Space Layout with Camera Positioning at Aisle Area" 132 shown in FIG. 12, two cameras can be placed at either ends of the aisle to capture the frontal face of people entering the aisle.

3. Entry Point Area: In the exemplary embodiment of the "Physical Space Layout with Camera Positioning at Entry Point Area" 133 shown in FIG. 12, multiple cameras can be placed in the entry point area. In the exemplary embodiment, the Entry point can be defined as the area where the people's traffic exists although the area may not be the hot spot in the physical space, such as the "Region of Interest (ROI) in Entry Point Area" 137 shown in FIG. 12.

4. Open Space Area: In the exemplary embodiment of the "Physical Space Layout with Camera Positioning at Open Space Area" 134 shown in FIG. 13, multiple cameras can be used to cover the "Region of Interest (ROI) in Open Space Area" 138. In a typical embodiment, the cameras are placed at the center of the space to be monitored, facing outwardly in the radial manner so that the collection of the camera fields-of-view covers the 360-degree span. In another possible embodiment where the space is cornered by walls, the cameras can be placed at the corner, to cover the 90-degree span as it is for the corner Entry Point Area.

In the exemplary camera positioning at open space 154 shown in FIG. 13, six cameras are used to cover the "Region of Interest (ROI) in Open Space Area" 138, so that the collection of each field-of-view, such as "field-of-view 1" 346 for the "means for capturing images 1" 110 and so on of the six cameras, can cover the 360-degree span.

Within each camera view, the region corresponding to the physical floor space of the area to be monitored is marked as the ROI (region of interest).

Figure 14:
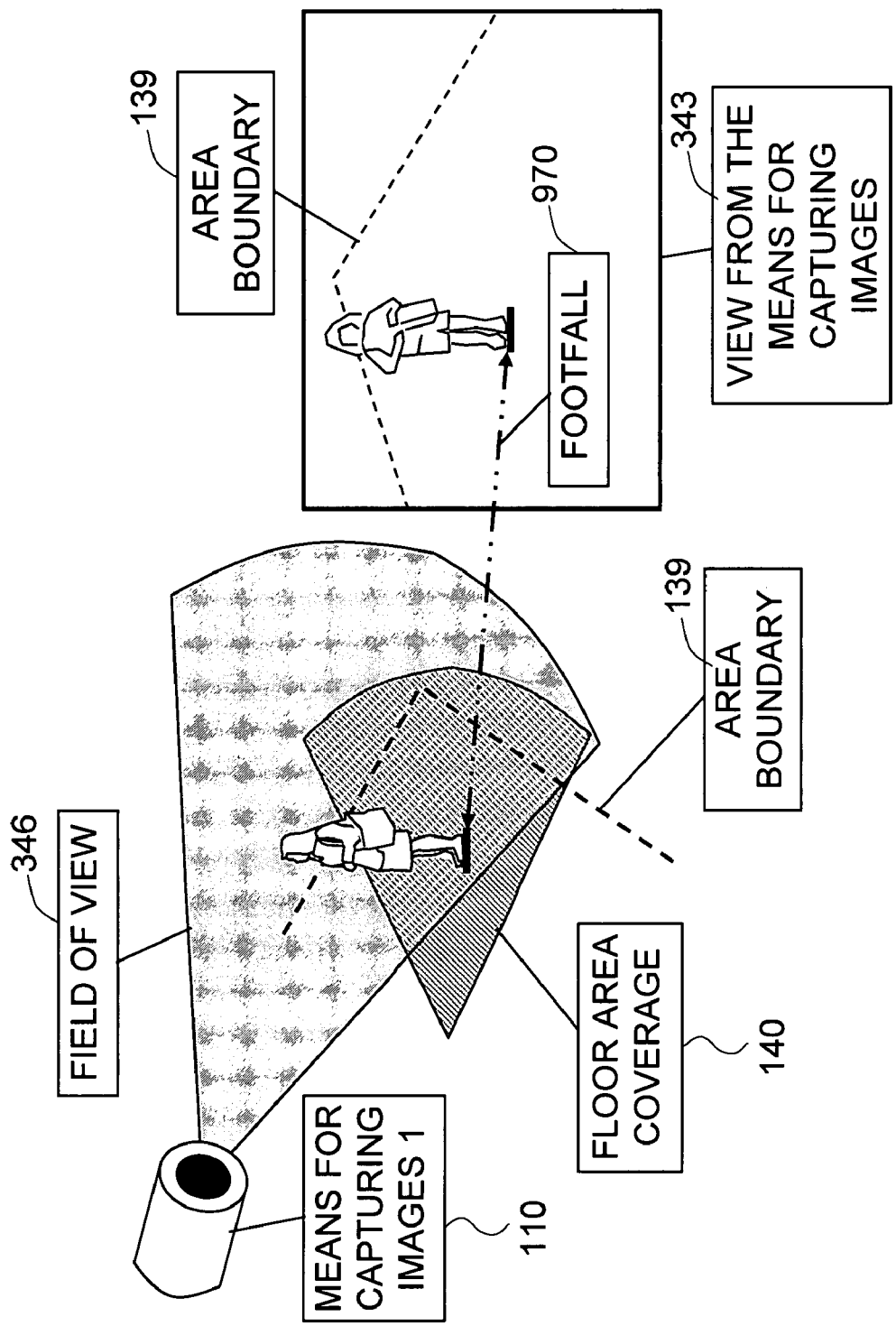
FIG. 14 shows exemplary relationship between the floor position in the physical world view and the image position in the view from the means for capturing images.

FIG. 14 shows exemplary relationship between the floor position in the physical world view and the image position in the "view from the means for capturing images" 343.

Given the position and the orientation of the means for capturing images, there is a one-to-one correspondence between the physical floor positions and the positions in the image. Therefore, it is possible to determine whether the detected person is dwelling in the target measurement area, by checking whether the footfall 970 position of the person is within the area boundary 139 in the image.

The Footfall Position Estimation

The bottom end of the segmented body image is marked as the footfall of the person. If the footfall of the person is within the ROI of the camera view, the person's facial image (and body image in some cases) is sent to the face detection & demographics classification module.

Figure 15:
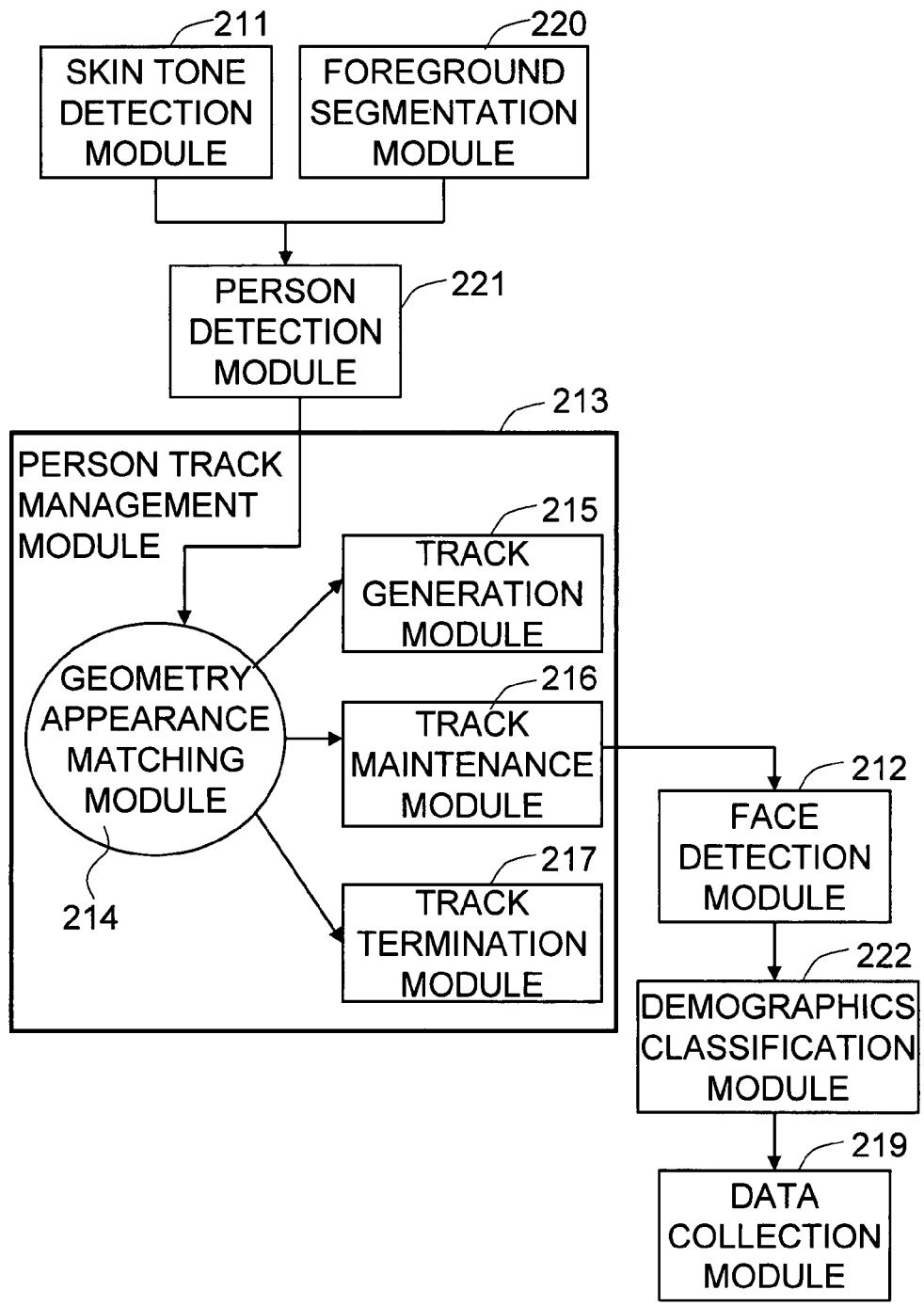
FIG. 15 shows exemplary software components in an exemplary embodiment of the present invention.

FIG. 15 shows exemplary software components in an exemplary embodiment of the present invention. The software components comprise the skin tone detection module 211, foreground segmentation module 220, person detection module 221, person track management module 213, face detection module 212, demographics classification module 222, and data collection module 219. The person track management module 213 further comprises geometry/appearance matching module 214, track generation module 215, track maintenance module 216, and track termination module 217.

The skin tone detection module 211 determines the region in the image frame that is similar to the human skin tone. The foreground segmentation module 220 finds the area in the image where any motion is taking place, so that the presence of a human body is likely. The person detection module 221 then runs the body detection window over the regions determined by the skin tone detection module 211 and the foreground segmentation module 220. The detected body images are first processed by the geometry/appearance matching module 214 to determine if the body images belong to the existing tracks or if some of the bodies are new, so that a new track can be generated. If the body is new, then the new track generation module 215 is activated to generate a new track and put it in the queue of tracks. If the body belongs to an existing track, then the track maintenance module 216 takes the track data. If the geometry/appearance matching module 214 cannot find subsequent bodies that belong to some track, then the track termination module 217 is activated to store the track data and remove the track from the memory queue. The face detection module 212 is activated to find possible frontal faces near the head area determined by the person detection module 221. The demographics classification module 222 then processes the body image or the face image to determine the demographic label of the person. The data collection module 219 then records the track data.

The data collection module 219 can further comprise a module for providing web-based reporting of the aggregated demographic characterization data, which enables a continuous access to the data on the web. The examples of the aggregated demographic characterization data can comprise visualization of the aggregated demographic characterization data. The continuous access is defined as the almost real-time access to the data with a certain delay.

The processing software component may be written in a high-level computer programming language, such as C++, and a compiler, such as Microsoft Visual C++, may be used for the compilation in the exemplary embodiment.

Figure 16:
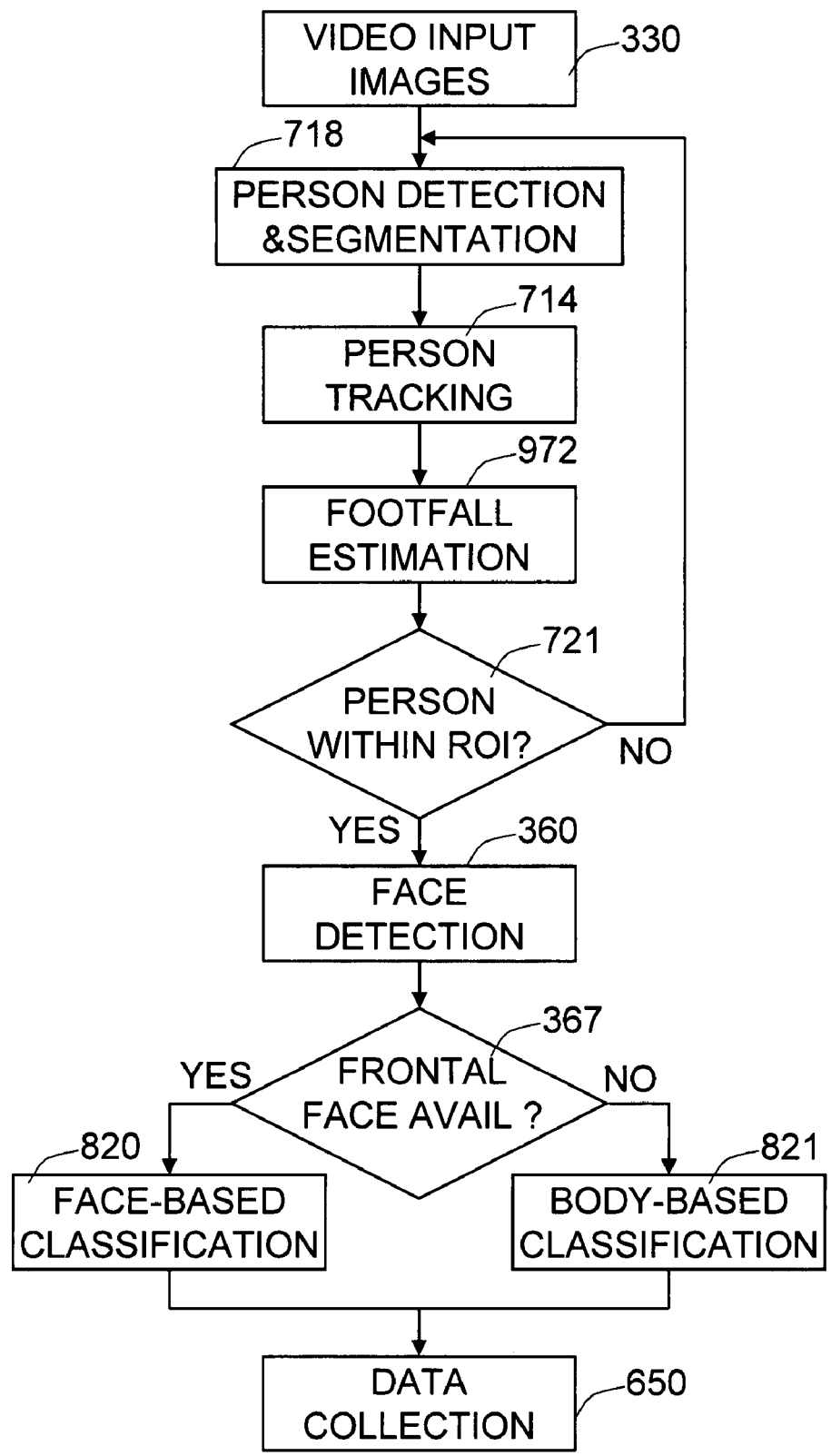
FIG. 16 shows exemplary processes in an exemplary embodiment of the present invention.

FIG. 16 shows exemplary processes in an exemplary embodiment of the present invention. The system of DBR aims to automatically measure the demographic composition of the audience in a predefined area in a physical space, by processing the video input images 330 from one or a plurality of means for capturing images. The system takes live video as an input, detects people in the area, and classifies the people's appearance into one of the demographics categories. The overview of the system is depicted in FIG. 16.

In the exemplary embodiment shown in FIG. 16, DBR processes "person detection and segmentation" 718 based on human body segmentation from the video input images 330. A combination of motion information and shape information or skin color can be employed to detect a person, and to segment out the body image in the exemplary embodiment. A machine learning based approach is employed to detect body parts, such as arms, legs, and torso. Each detection scores are aggregated to give the whole body detection score. One of machine learning schemes that can represent and capture geometric and semantic structure of the human body (e.g., HMM or graphical model) may be used. Because the people's body pose is constrained to some degree (standing or walking), the problem is more tractable than a generic body detection problem.

The DBR then processes person tracking 714 for keeping track of the detected people. The tracking step in track management of the DBR serves as a means to keep the identity of a person in the scene. The system can then accumulate the person classification scores across the person's body appearance in the person track, so that the classification accuracy is further improved. In the exemplary embodiment, the tracking can utilize two measurements; the geometric and appearance match between the track history and the newly detected body. The track management in the exemplary embodiment of the DBR will be explained further in regards to FIG. 18.

In the exemplary embodiment, the DBR uses the footfall position estimation 972 to send the person's facial image (and body image, in some cases) to the face detection & demographics classification module if the footfall of the person is within the ROI 721 of the camera view.

Based on the detected body location, face detection 360 is performed around the expected head position. A machine learning based approach is employed to detect faces, and the step provides the system with the locations and sizes of detected faces in the given video frame.

If the face detection 360 step determines that the frontal face image is available 367, the classifier can use the face image to determine the person's demographics group. A machine learning based approach can be employed to compute the score (likelihood) that the given face image belongs to each demographics category in the face-based demographics classification 820.

If the face detection 360 step does not detect a frontal face, the demographics classification can be performed utilizing the bodily appearance 821. The body appearance (hairstyle, clothing, build) can be trained to give classification scores from the machine learning method similar to face classification. The upright body pose constrains the problem nicely than in general cases where people can have unconstrained poses.

The DBR stores 650 the demographic composition data, and the data is accessible by the programming module, so that the system can directly and automatically utilize the demographics composition data for the characterization of the physical space. On the other hand, the data can also be available to the decision maker of a particular physical space, so that the decision maker can characterize the physical space based on the demographics composition data.

Figure 17:
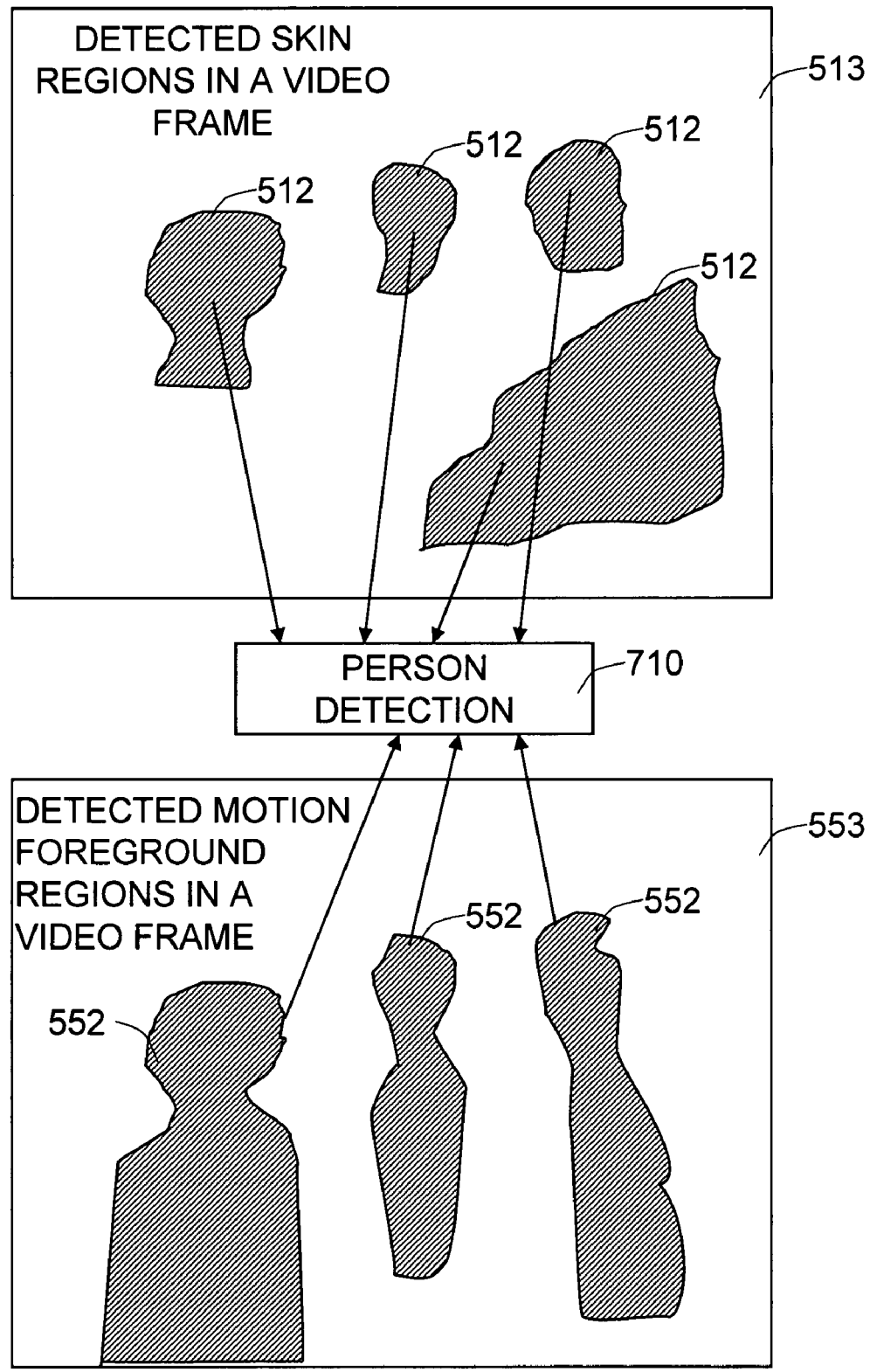
FIG. 17 shows exemplary body detection and segmentation in the exemplary embodiment.

FIG. 17 shows exemplary body detection and segmentation in the exemplary embodiment. For the body detection and segmentation, a combination of motion information and shape information can be employed to detect a person, and to segment out the body image. The exemplary embodiment in FIG. 17 shows an exemplary method for segmenting the skin region for person detection 710.

In the exemplary embodiment, the DBR first processes the skin tone segmentation 513. At the skin tone segmentation 513 step, the module first segments out the area in the video frame where the human body parts, such as faces, are likely to be present, using color information. The scheme utilizes a color space transformation, so that the skin tone forms a compact region in the transformed space. The skin tone detection serves as a means to speed up the person detection 710. The output from this step is a collection of masked regions, for the detected skin region 512, in the video frame.

The motion foreground segmentation 553 is performed independent of the skin tone segmentation 513, to determine the area, motion foreground 552, where the image pixel values change due to the motion of people. The step serves as a means to reduce the search space for person detection and also to reduce the number of falsely detected person images. In the exemplary embodiment, the motion foreground detection is performed by building the temporal background model and thresholding out the region (as the motion foreground) where the pixel value changes exceed the threshold determined by the background model.

For the person detection 710 process, a machine learning based approach may be employed to detect human body parts, such as faces, within the skin tone and motion foreground region determined by the previous step. This step can operate on an image converted to gray scale to detect body images. The step provides the system with the locations and sizes of detected people in the given video frame.

Figure 18:
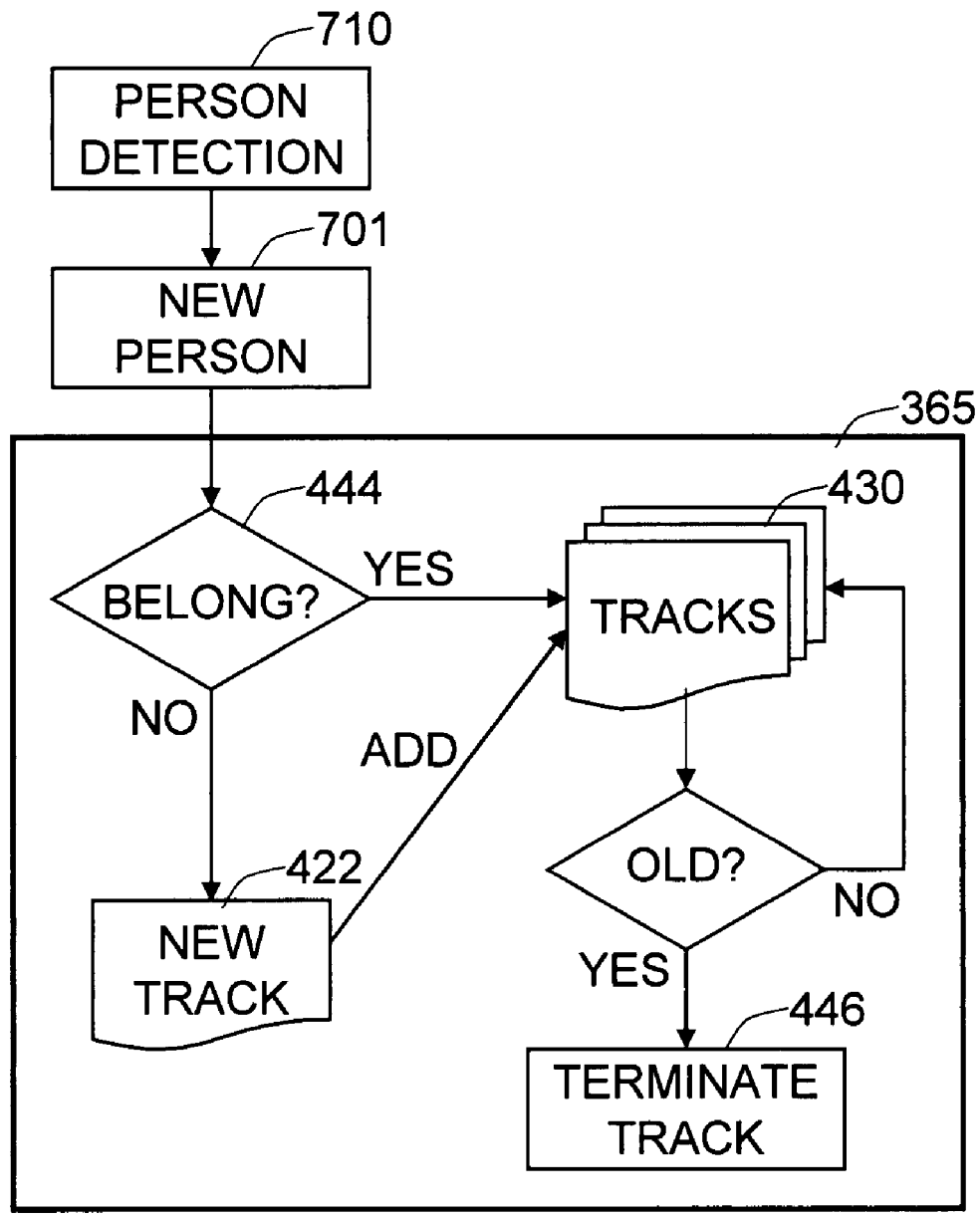
FIG. 18 shows an exemplary person tracking, verification, and track management in an exemplary embodiment.

FIG. 18 shows an exemplary person tracking, verification, and track management in an exemplary embodiment.

People Tracking and Verification

The tracking step serves as a means to keep the identity of a person in the scene. The system can then accumulate the person classification scores across the person's body appearance in the person track, so that the classification accuracy is further improved.

In the exemplary embodiment shown in FIG. 18, the tracking can utilize two measurements; the geometric and appearance match between the track history and the newly detected body. The track management serves as a means to generate a track when a new person 701 appears in the scene through person detection 710, assign detected body image to tracks to keep identities of people, and to terminate 446 a track when the person is out of the scene.

When new bodies are detected in the current video frame, the track management constructs a table of bodies and tracks. Then it computes the geometric match and appearance match scores of each (body, track) pair that measure the likelihood of the given body belonging 444 to the given track in the person track verification 365 process.

The geometric match score is based on difference in the position, size, and the time between the new body and the last body in the track.

The appearance match score measures the similarity between the model body appearance stored in the track, and the new body, using the color composition and the shape of the body appearance. If the total score (geometric+appearance) is below a predetermined threshold, the pair is excluded from the table. The pair having the highest score gets the assignment: from body to track, body→track. The procedure is repeated until all the faces are assigned matching tracks.

However, if there is a new person in the scene, the body appearance is not supposed to have a match to existing tracks. In that case the threshold should have excluded the body image, and the body should remain in the queue. The body image then generates a new track 422, and the track is added to the list of tracks 430. For every frame, if a certain track did not have a new body image for more than a pre-specified time period, the track management terminates 446 the track.

The Footfall Position Estimation

The bottom end of the segmented body image is marked as the footfall of the person. If the footfall of the person is within the ROI of the camera view, the person's facial image (and body image, in some cases) is sent to the face detection & demographics classification module.

Face Detection

Based on the detected body location, face detection is performed around the expected head position. The face can be detected or not, depending on the facial orientation of the person.

In the exemplary embodiment, a machine learning based approach can be employed to detect faces, such as artificial neural network based or AdaBoost-based face detectors. Typically thousands of facial images are necessary to train these face detectors to robustly detect human faces in real-world videos. This step can operate on an image converted to gray scale to detect faces. The step can provide the system with the locations and sizes of detected faces in the given video frame.

Demographics Classification Using Facial Image

If the face detection step determines that the frontal face image is available, the classifier can use the face image to determine the person's demographics group. In the exemplary embodiment, a machine learning based approach can be employed to compute the score (likelihood) that the given face image belongs to each demographics category.

Figure 19:
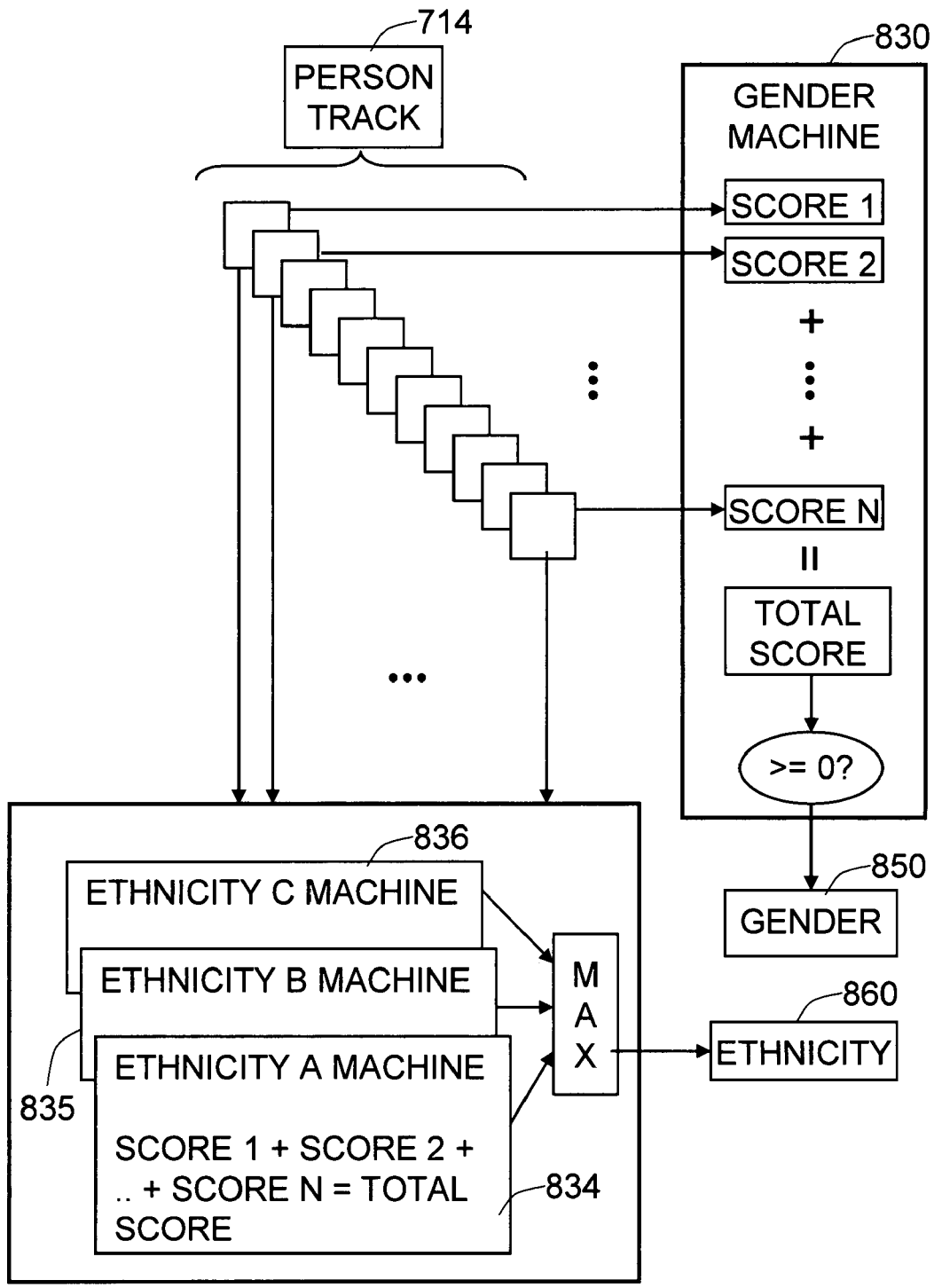
FIG. 19 shows an exemplary face classification based on gender and ethnicity in an exemplary embodiment of the present invention.

FIG. 19 shows an exemplary face classification based on gender 850 and ethnicity 860 in an exemplary embodiment of the DBR.

Gender Classification

In the exemplary embodiment, a machine learning based classifier, gender machine 830, may be used for gender recognition. Face images are used for training the learning machine for gender classification; the test faces go through the same procedure as the training faces. In the exemplary embodiment, the classifier (the learning machine) is trained to output the gender score: −1 for female and +1 for male.

The tracking stage will group individual faces into person tracks; each person track is assigned a gender label by adding up the gender scores of the faces belonging to the track. If the accumulated score is negative, then the person is labeled as female, and if the accumulated score is positive, then the person is labeled as male.

Ethnicity Classification

In the exemplary embodiment of the DBR shown in FIG. 19, the system can classify the faces into designated classes of ethnic groups. The system can employ the same number of learning machines as the number of ethnic groups. Each learning machine is tuned to the given ethnic group; for example, when there are three (A, B, C) ethnic groups, the "learning machine for ethnicity A" 834 is trained to output +1 for the faces from group A, and −1 for faces from groups B or C. The "learning machine for ethnicity B" 835 is trained to output +1 for the faces from group B, and −1 for faces from groups A or C. Likewise, the "learning machine for ethnicity C" 836 is trained to output +1 for the faces from group C, and −1 for faces from groups A or B.

The input face image is fed to all the learning machines, and the machines output scores. As in the gender classification, the scores from all the faces in the person track are added up. The accumulated gender score of the person track provides a more reliable ethnicity signature of the person's face than the individual scores do.

The rule of decision is that when a given face has a positive score from the learning machine A, then the face is classified as belonging to the ethnic group A. There can be cases where a face will have positive scores for more than one class. The DBR can resolve the ambiguity by assigning the ethnic group having the maximum score to the face in the exemplary embodiment.

Although FIG. 19 shows an exemplary face classification based on gender and ethnicity attributes in an exemplary embodiment of the DBR, the described computer vision technologies can be applied to other face classification attributes, such as age, based on the visual information from the face captured by the means for capturing images 100.

Demographics Classification Using Bodily Appearance

If the face detection step does not detect a frontal face, the demographics classification can be performed utilizing the bodily appearance in the exemplary embodiment. In the exemplary embodiment, a machine learning based approach can be employed to detect body parts, such as arms, legs, and torso. Each detection scores are aggregated to give the whole body detection score. A machine learning scheme that can represent and detect geometric and semantic structure of the body (e.g., HMM or graphical model) may be used. Because the people's body pose is constrained to some degree (standing or walking), the problem is more tractable than a generic body detection problem.

In the exemplary embodiment, the body appearance (hairstyle, clothing, build) can be trained to give classification scores from the machine learning method similar to face classification. The upright body pose constrains the problem more nicely than in general cases where people can have unconstrained poses.

Figure 20:
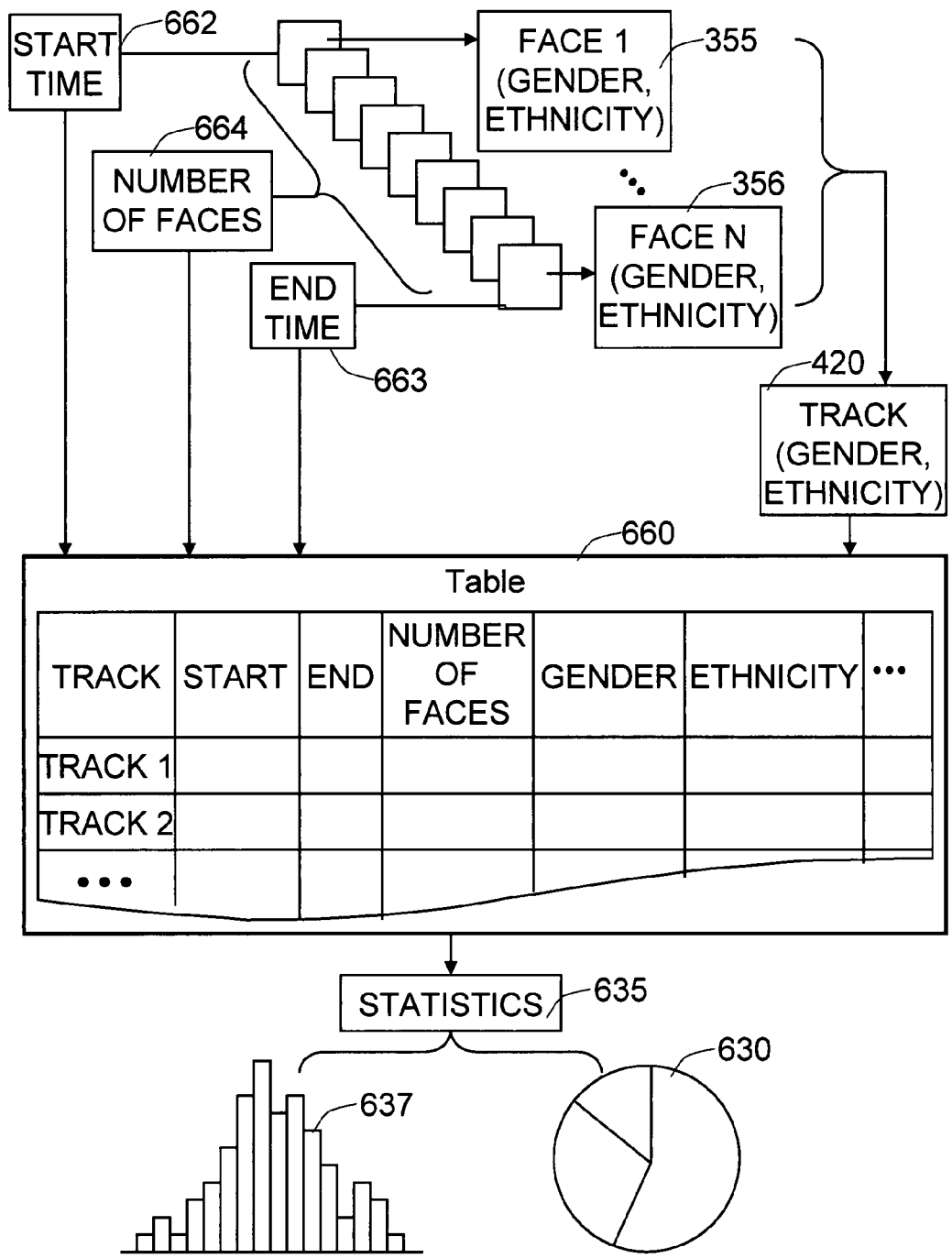
FIG. 20 shows an exemplary data storage process in an exemplary embodiment of the present invention.

FIG. 20 shows an exemplary data storage process in an exemplary embodiment of the DBR. In the exemplary embodiment, the system stores the data as a table 660, where each track has fields of values: time stamps (start time 662 for person appearance and end time 663 for person disappearance) based on face 1 355 and face N 356, the number of faces 664, and gender 850 and ethnicity 860 labels. The exemplary data can be used to collect statistics 635 of gender and ethnic composition of the audience, and the statistics 635 can be represented as a pie chart 630, as a bar graph 637, or any data representation means in the exemplary embodiment. The data is accessible by the programming module, so that the system can directly and automatically utilize the demographics composition data for the characterization of the physical space.

While the above description contains much specificity, these should not be construed as limitations on the scope of the invention, but as exemplifications of the presently preferred embodiments thereof. Many other ramifications and variations are possible within the teachings of the invention. Thus, the scope of the invention should be determined by the appended claims and their legal equivalents, and not by the examples given.

What is claimed is:

1. A method for characterizing a physical retail space based on automatic measurement of a demographic composition of a plurality of shoppers in the physical retail space, comprising the following steps of:
   a) dividing said physical retail space into a plurality of sub-regions, the sub-regions comprising at least one of aisles, entry points, exit points, or predefined areas of said physical retail space,
   b) capturing a plurality of input video images of said plurality of shoppers in said physical retail space and said retail space sub-regions over a specified period of time by a plurality of cameras,
   c) automatic measuring demographic information of each shopper in said plurality of shoppers in said plurality of input video images using a computer, said demographic information comprising age, gender and ethnicity information,
   d) determining statistics of said demographic information and measuring said demographic composition of said plurality of shoppers in said physical retail space and said retail space sub-regions, said demographic composition comprising categories defining entity with a group of products, a group of product types, spaces, areas or display of a group of products, and
   e) characterizing said physical retail space and said retail space sub-regions based on said demographic measuring and said demographic statistics, said physical retail space characterization comprising at least one of the following:
      a characterization of said demographic composition of shoppers in said physical retail space and retail space sub-regions; or
      a characterization of said physical retail space or said retail space sub-regions by product match or media match based on said demographic composition; or
      a characterization of said physical retail space and retail space sub-regions according to a media effectiveness measurement based on said demographic composition measuring; and
   f) outputting, by a computer, said physical retail space characterization of said physical retail space and retail space sub-regions.

2. The method according to claim 1, wherein the method further comprises a step of repeating the steps from a) to d) for a plurality of physical spaces in a network of spaces,
   whereby said network of spaces comprises a large number of stores.

3. The method according to claim 1, wherein the method further comprises a step of taking samples from the universe of the plurality of shoppers for measuring the statistics of demographic information,
   wherein the step of characterizing said physical space uses the sample statistics of demographic information.

4. The method according to claim 1, wherein the method further comprises a step of dividing said physical space into a plurality of sub-regions and characterizing said physical space per sub-region based on the demographic statistics and composition in each sub-region of said plurality of sub-regions in said physical space.

5. The method according to claim 1, wherein the method further comprises a step of re-zoning said physical space based on the demographic characterization in said physical space.

6. The method according to claim 1, wherein the method further comprises a step of measuring a pattern of changes in demographics due to changes in the product match or media match as a part of the physical space characterization.

7. The method according to claim 1, wherein the method further comprises a step of measuring media effectiveness based on the demographic characterization of said physical space,
   whereby the measurement of the media effectiveness is achieved by analyzing what drives the plurality of shoppers in a certain demographic composition to buy a certain category of products.

8. The method according to claim 1, wherein the method further comprises a step of enabling actual verification of demographic composition for the physical space characterization, by measuring the demographic composition for those who actually visited the physical space.

9. The method according to claim 1, wherein the method further comprises a step of applying the physical space characterization to different servicing strategies, so that the application attracts a specific demographic group, based on the actually measured demographic data, by matching needs for the specific demographic group.

10. The method according to claim 1, wherein the method further comprises a step of providing web-based reporting of an aggregated demographic characterization data,
  whereby the aggregated demographic characterization data comprises visualization of the aggregated demographic characterization data.

11. The method according to claim 1, wherein the method further comprises a step of positioning said plurality of cameras near an entrance and exit or a plurality of entrances and exits in said physical space,
  wherein an aggregated measurement of the demographic composition at all of the entrances and exits of the physical space provides a solution for characterizing the entire physical space.

12. The method according to claim 1, wherein the method further comprises a step of positioning said plurality of cameras in the vicinity of a plurality of aisles in said physical space,
  wherein the physical space characterization is performed to characterize the aisles, and wherein the demographic composition measurement at the vicinity of the plurality of aisles provides information for finer level of interest of the demographics for particular products at the specific aisle area.

13. The method according to claim 1, wherein the method further comprises a step of placing said plurality of cameras in a place within a predefined open space where a plurality of the fields of view from said plurality of cameras cover said predefined open space, wherein the physical space characterization is performed to characterize the predefined open space.

14. The method according to claim 1, wherein the method further comprises a step of automatically delimiting a predefined area in the views of said plurality of cameras, so that the method selects and processes only the faces of said plurality of shoppers dwelling in the delimited predefined area,
  wherein placement of the cameras is dependent on the kind of physical space that needs to be characterized.

15. The method according to claim 1, wherein the method further comprises a step of positioning said plurality of cameras in the vicinity of a plurality of entry points in said physical space,
  wherein the physical space characterization is performed to characterize the entry points, and wherein an entry point is defined as an area where people's traffic exists although the area is not a hot spot in a physical space.

16. The method according to claim 1, wherein the method further comprises a step of segmenting body images of each shopper of said plurality of shoppers in the captured plurality of input images, so that the physical floor position of said each shopper is estimated,
  whereby a lowest end of the segmented body image is marked as the footfall of said each shopper,
  whereby when the footfall of said each shopper is within the region of interest in the views of said plurality of cameras, the shopper's facial image and body image are sent to a demographics classification module, and
  whereby when the footfall of said each shopper is not within the region of interest in the views of said plurality of cameras, the shopper's facial image and body image are not sent to a demographics classification module.

17. The method according to claim 1, wherein the method further comprises a step of segmenting out the regions having human skin-like color pixel values in the captured plurality of input images.

18. The method according to claim 1, wherein the method further comprises a step of detecting faces of said plurality of shoppers in a crowded and complex indoor scene and a step of providing the locations and sizes of detected faces.

19. The method according to claim 1, wherein the method further comprises a step of detecting locations of facial features and estimating the position, size, and orientation of a facial image detected from a face detection scheme.

20. The method according to claim 1, wherein the method further comprises a step of aligning a facial image detected from a face detection step using a facial geometry estimation.

21. The method according to claim 20, wherein the method further comprises a step of automatically classifying the gender of a shopper in said plurality of shoppers based on a gender score of an aligned face image.

22. The method according to claim 20, wherein the method further comprises a step of automatically classifying the ethnicity of a shopper in said plurality of shoppers among multiple designated classes of ethnicity based on an ethnicity score of an aligned facial image.

23. The method according to claim 20, wherein the method further comprises a step of automatically classifying the age of a shopper in said plurality of shoppers among multiple designated classes of age groups based on an age score of an aligned facial image.

24. An apparatus for characterizing a physical retail space based on automatic measurement of a demographic composition of a plurality of shoppers in the physical retail space, comprising:
  a) means for dividing said physical retail space into a plurality of sub-regions, the sub-regions comprising at least one of aisles, entry points, exit points, or predefined areas of said physical retail space,
  b) means for capturing a plurality of input video images of said plurality of shoppers in said physical retail space and said retail space sub-regions over a specified period of time by a plurality of means for capturing images,
  c) means for automatic measuring demographic information of each shopper in said plurality of shoppers in said plurality of input video images using a means for control and processing, said demographic information comprising age, gender and ethnicity information,
  d) means for determining statistics of said demographic information and measuring said demographic composition of said plurality of shoppers in said physical retail space and said retail space sub-regions, said demographic composition comprising categories defining entity with a group of products, a group of product types, spaces, areas or display of a group of products, and
  e) means for characterizing said physical retail space and said retail space sub-regions based on said demographic measuring and said demographic statistics, said physical retail space characterization comprising at least one of the following:
    a characterization of said demographic composition of shoppers in said physical retail space and retail space sub-regions; or
    a characterization of said physical retail space or said retail space sub-regions by product match or media match based on said demographic composition; or a characterization of said physical retail space and retail space sub-regions according to a media effectiveness measurement based on said demographic composition measuring; and f) means for outputting said physical retail space characterization of said physical retail space and retail space sub-regions.

25. The apparatus according to claim 24, wherein the apparatus further comprises means for repeatedly using the means from a) to d) for a plurality of physical spaces in a network of spaces, whereby said network of spaces comprises a large number of stores.

26. The apparatus according to claim 24, wherein the apparatus further comprises means for taking samples from the universe of the plurality of shoppers for measuring the statistics of demographic information, wherein the means for characterizing said physical space uses the sample statistics of demographic information.

27. The apparatus according to claim 24, wherein the apparatus further comprises means for dividing said physical space into a plurality of sub-regions and characterizing said physical space per sub-region based on the demographic statistics and composition in each sub-region of said plurality of sub-regions in said physical space.

28. The apparatus according to claim 24, wherein the apparatus further comprises means for re-zoning said physical space based on the demographic characterization in said physical space.

29. The apparatus according to claim 24, wherein the apparatus further comprises means for measuring a pattern of changes in demographics due to changes in the product match or media match as a part of the physical space characterization.

30. The apparatus according to claim 24, wherein the apparatus further comprises means for measuring media effectiveness based on the demographic characterization of said physical space, whereby the measurement of the media effectiveness is achieved by analyzing what drives the plurality of shoppers in a certain demographic composition to buy a certain category of products.

31. The apparatus according to claim 24, wherein the apparatus further comprises means for enabling actual verification of demographic composition for the physical space characterization, by measuring the demographic composition for those who actually visited the physical space.

32. The apparatus according to claim 24, wherein the apparatus further comprises means for applying the physical space characterization to different servicing strategies, so that the application attracts a specific demographic group, based on the actually measured demographic data, by matching needs for the specific demographic group.

33. The apparatus according to claim 24, wherein the apparatus further comprises means for providing web-based reporting of an aggregated demographic characterization data, whereby the aggregated demographic characterization data comprises visualization of the aggregated demographic characterization data.

34. The apparatus according to claim 24, wherein the apparatus further comprises means for positioning said plurality of means for capturing images near an entrance and exit or a plurality of entrances and exits in said physical space, wherein an aggregated measurement of the demographic composition at all of the entrances and exits of the physical space provides a solution for characterizing the entire physical space.

35. The apparatus according to claim 24, wherein the apparatus further comprises means for positioning said plurality of means for capturing images in the vicinity of a plurality of aisles in said physical space, wherein the physical space characterization is performed to characterize the aisles, and wherein the demographic composition measurement at the vicinity of the plurality of aisles provides information for finer level of interest of the demographics for particular products at the specific aisle area.

36. The apparatus according to claim 24, wherein the apparatus further comprises means for placing said plurality of means for capturing images in a place within a predefined open space where a plurality of the fields of view from said plurality of means for capturing images cover said predefined open space, wherein the physical space characterization is performed to characterize the predefined open space.

37. The apparatus according to claim 24, wherein the apparatus further comprises means for automatically delimiting a predefined area in the views of said plurality of means for capturing images, so that the apparatus selects and processes only the faces of said plurality of shoppers dwelling in the delimited predefined area, wherein placement of the means for capturing images is dependent on the kind of physical space that needs to be characterized.

38. The apparatus according to claim 24, wherein the apparatus further comprises means for positioning said plurality of means for capturing images in the vicinity of a plurality of entry points in said physical space, wherein the physical space characterization is performed to characterize the entry points, and wherein an entry point is defined as an area where people's traffic exists although the area is not a hot spot in a physical space.

39. The apparatus according to claim 24, wherein the apparatus further comprises means for segmenting body images of each shopper of said plurality of shoppers in the captured plurality of input images, so that the physical floor position of said each shopper is estimated, whereby a lowest end of the segmented body image is marked as the footfall of said each shopper, whereby when the footfall of said each shopper is within the region of interest in the views of said plurality of means for capturing images, the shopper's facial image and body image are sent to a demographics classification module, and whereby when the footfall of said each shopper is not within the region of interest in the views of said plurality of means for capturing images, the shopper's facial image and body image are not sent to a demographics classification module.

40. The apparatus according to claim 24, wherein the apparatus further comprises means for segmenting out the regions having human skin-like color pixel values in the captured plurality of input images.

41. The apparatus according to claim 24, wherein the apparatus further comprises means for detecting faces of said plurality of shoppers in a crowded and complex indoor scene and means for providing the locations and sizes of detected faces.

42. The apparatus according to claim 24, wherein the apparatus further comprises means for detecting locations of facial features and estimating the position, size, and orientation of a facial image detected from a face detection scheme.

43. The apparatus according to claim 24, wherein the apparatus further comprises means for aligning a facial image detected from a face detection using a facial geometry estimation.

44. The apparatus according to claim 43, wherein the apparatus further comprises means for automatically classifying the gender of a shopper in said plurality of shoppers based on a gender score of an aligned face image.

45. The apparatus according to claim 43, wherein the apparatus further comprises means for automatically classifying the ethnicity of a shopper in said plurality of shoppers among multiple designated classes of ethnicity based on an ethnicity score of an aligned facial image.

46. The apparatus according to claim 43, wherein the apparatus further comprises means for automatically classifying the age of a shopper in said plurality of shoppers among multiple designated classes of age groups based on an age score of an aligned facial image.

* * * * *